United States Patent [19]

Adler et al.

[11] Patent Number: 4,609,388
[45] Date of Patent: Sep. 2, 1986

[54] GAS SEPARATION PROCESS

[75] Inventors: Robert J. Adler, Shaker Heights; Coleman B. Brosilow, Cleveland Heights; William R. Brown, Brecksville; Nelson C. Gardner, Cleveland Heights, all of Ohio

[73] Assignee: CNG Research Company, Pittsburgh, Pa.

[21] Appl. No.: 737,579

[22] Filed: May 24, 1985

Related U.S. Application Data

[63] Continuation of Ser. No. 196,124, Oct. 9, 1980, abandoned, which is a continuation-in-part of Ser. No. 31,318, Apr. 18, 1979, Pat. No. 4,270,937, which is a continuation-in-part of Ser. No. 746,622, Dec. 1, 1976, abandoned.

[51] Int. Cl.$^4$ .................................................. F25J 3/00
[52] U.S. Cl. .......................................... 62/12; 55/68; 55/73; 62/17; 62/20; 62/532
[58] Field of Search ............ 62/24, 27, 28, 17, 12–16, 62/22, 20, 532–535, 536, 537, 541; 55/73, 68

[56] References Cited

U.S. PATENT DOCUMENTS 3,417,572 12/1968 Pryor ...................................... 62/17
3,643,451 2/1972 Foucar ................................... 62/28

*Primary Examiner*—Frank Sever
*Attorney, Agent, or Firm*—Pearne, Gordon, Sessions, McCoy, Granger & Tilberry

[57] ABSTRACT

A process for separating acid gases such as $CO_2$, $H_2S$, and $SO_2$, other sulfur-containing molecules such as COS, and other relatively high boiling point impurities from lower boiling point components of a gas stream comprises: dehydrating the gas stream and contacting it, at an elevated pressure and at substantially the dew point temperature of carbon dioxide therein, with a liquid carbon dioxide refrigerant-absorbent to absorb such impurities other than $CO_2$, and separating the liquid carbon dioxide and absorbed impurities; condensing $CO_2$, and separating the liquid carbon dioxide and absorbed impurities; and condensing $CO_2$ from the residual gas stream at such pressure, preferably by indirect heat exchange. A crystallization process is also disclosed for separating the liquid carbon dioxide and absorbed impurities. The residual gas stream obtained following indirect heat exchange may be processed further by contact with a second refrigerant-absorbent which preferably comprises a liquid-solid slurry. Further, a crystallization process is disclosed for separating a crystallizable material and an excluded material which is at least partially excluded from the solid phase of the crystallizable material obtained upon freezing a liquid mixture of the materials. The solid phase is formed and melted at spaced locations in a liquid mixture of the materials and, within the liquid mixture, internal solid and liquid flows are maintained in opposite directions to effect separation of the materials. The solid phase is formed by evaporative cooling of the liquid mixture and melted by direct contact with a condensing vapor phase of the materials, each of these operations being performed substantially at the prevailing triple point locus conditions in the respective locations in the liquid mixture.

44 Claims, 8 Drawing Figures

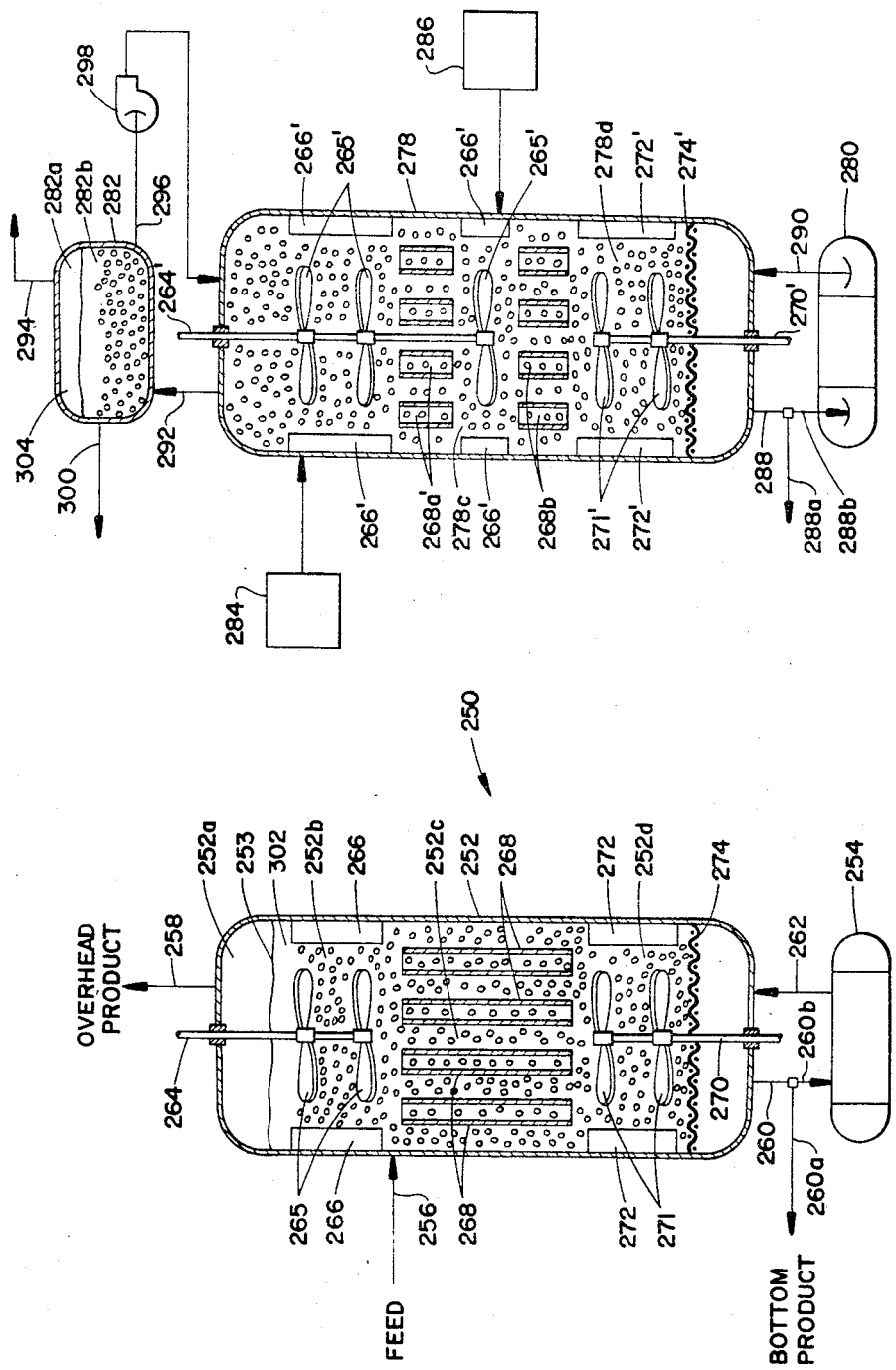

GAS SEPARATION PROCESS

This is a continuation of application Ser. No. 196,124, filed on Oct. 9, 1980, now abandoned, which in turn is a continuation-in-part of applicants' copending application Ser. No. 31,318, filed Apr. 18, 1979, now U.S. Pat. No. 4,270,937, issued June 2, 1981, which in turn is a continuation-in-part of applicants' then copending application Ser. No. 746,622, filed Dec. 1, 1976, now abandoned.

BACKGROUND OF THE INVENTION

This invention relates to the selective removal of acid gases such as carbon dioxide, hydrogen sulfide, and sulfur dioxide, other sulfur-containing compounds such as carbonyl sulfide, and other relatively high boiling point gases, generally regarded as contaminants, from gas mixtures also containing lower boiling point components such as hydrogen, carbon monoxide, methane, and other light molecules such as nitrogen, some or all of which may be of primary value. The invention has particular application to the selective removal of acid gases and other sulfur-containing gases from, for example, the gaseous products of coal gasification, so as to produce a fuel gas end product of enhanced value and utility. The invention is particularly useful also in the selective removal of similar contaminants from the products of combustion of methane or other carbon-containing fuels to produce hydrogen and nitrogen in the manufacture of ammonia. A simplified form of the invention has particular application to the removal of sulfur-containing compounds and also suspended particulate matter from stack or flue gases. Various other uses for the invention will be recognized by those skilled in the art.

This invention also relates to a novel process for crystallization of a component of a fluid mixture by freezing. This crystallization process is useful as a part of the main gas separation process referred to above and is also adapted for more general use to separate a material that is crystallizable by freezing from other material. For example, this novel crystallization process may be used to separate carbon dioxide from hydrogen sulfide in the main gas separation process referred to above to provide substantially pure carbon dioxide and relatively concentrated hydrogen sulfide. In addition, by way of further illustration, it may be used to separate the isomers of xylene, ethane from carbon dioxide, or sulfur hexafluoride from hydrogen sulfide and/or light hydrocarbons. This novel crystallization process may be performed as a batch process or as a continuous process.

Many methods have been developed for effecting the selective separation of acid gases from other gases of primary value. Usually, a chemical or physical absorbent for the acid gases to be separated is contacted by the gas mixture being treated, the absorbent and absorbed acid gases are separated, and the absorbent is regenerated and recycled. The Benfield hot carbonate process is a typical example of processes using chemical absorption. See *Pipeline and Gas Journal*, Oct. 19, 1972, p. 58. The Rectisol refrigerated methanol process is a typical example of processes using physical absorption. See *Industrial and Engineering Chemistry*, July 1970, pp. 39–43.

Particularly in the case of chemical absorption processes, but also to a substantial degree in the case of most physical absorption processes, there are substantial, inherent irreversibilities in both the absorption and regeneration steps. These irreversibilities necessitate substantial energy inputs to the processes. For example, in the Benfield hot carbonate process, substantial amounts of steam are needed to regenerate the alkaline carbonate solution employed as the absorbent. And, in the Rectisol refrigerated methanol process, substantial amounts of steam and refrigeration are needed to regenerate the methanol absorbent. Thus, an undesirable characteristic of prior acid gas removal processes is their inherent, substantial energy consumption in regenerating the absorbent.

In many of the prior gas separation processes, the absorbent streams gradually accumulate impurities that have no value and would cause objectionable pollution if discharged into the environment. In those cases, additional capital and operating costs must be incurred for processing contaminated absorbent bleed or slip streams. Many of the prior gas separation processes also inherently involve substantial losses of absorbents due to minor poisoning reactions, leaks, thermal degradation, evaporation into the purified gases, and the slow accumulation therein of tars and other heavy materials. Make-up for these absorbent losses represents a continuous operating cost.

Another undesirable characteristic of many prior acid gas removal processes is that they require high capital and operating costs to recover the separated hydrogen sulfide and other sulfurcontaining gases in a sufficiently high concentration for economical processing in a Claus plant to reduce them to elemental sulfur and non-polluting wastes. See *Hydrocarbon Processing*, April 1971, p. 112.

Another undesirable characteristic inherent in some of the prior gas separation processes is that they require the use of absorbent solutions that are corrosive or become corrosive in use. This requires periodic replacement of equipment or the use of expensive corrosion-resistant materials or expensive corrosion inhibiting chemicals.

Another disadvantage of many prior gas separation processes is that much of the available pressure and thermal energy of the purified gas stream and of the separated gases and reagents is not recovered. More reversible processes could recover and utilize such potentially available energy.

Another disadvantage of many prior gas separation processes is that they use relatively viscous absorbents or reagents, which decrease absorber stage efficiency and consume significant amounts of energy for pumping.

Another disadvantage of most prior gas absorption processes is that expensive heat exchangers or excessive absorbent flows are necessary to remove heat of absorption when large amounts of gas are absorbed.

Still another undesirable characteristic inherent in some of the prior acid gas removal processes is their inability to remove trace impurities that are undesirable in the purified product gases. Typical trace materials, depending on the sources of the gases to be purified, may include metal carbonyls and sulfurcontaining molecules (other than hydrogen sulfide), such as carbonyl sulfide, carbon disulfide, mercaptans, and the like, relatively high boiling nitrogen-containing compounds, including ammonia and hydrogen cyanide, and relatively high boiling hydrocarbons (as hereinafter defined). The inability to remove such trace impurities results in end product gases of lesser value or reduced utility. Of the various trace impurities encountered in acid gas removal processes, carbonyl sulfide is particularly objectionable and generally must be removed if present in a gas stream being treated. Some prior acid gas removal processes are incapable of doing so without substantially increasing absorbent flows, which requires large additional capital and operating costs.

To the extent that prior art crystallization techniques are employed in such prior acid gas removal processes, there are additional disadvantages associated with known crystallization processes which are briefly described below.

Crystallization is potentially an attractive method of separating the components of a system or mixtures of materials, since impurity concentrations in the crystals are typically one tenth, one one-hundredth, or even a lesser fraction of the impurity concentration in the mother liquor. Thus, a few recrystallizations can often produce a highly purified product. However, crystallization processes used to date have certain practical shortcomings which limit their more widespread use. In many conventional crystallization processes, the crystals are formed by freezing on heat exchange surfaces which are scraped (mechanically) to remove the crystals. The crystals are then conveyed to a washing zone and separated from the liquid. Melting is accomplished by supplying heat through heat exchange surfaces. The heat exchange surfaces needed for freezing and melting and the mechanical scraping and conveying equipment are costly and troublesome.

In some improved crystallization processes, certain of the foregoing disadvantages are overcome by using an in situ refrigerant to form the crystals. Evaporation of refrigerant from the liquid mixture produces crystals directly. This type of process has the advantage of eliminating heat exchange surfaces for cooling, but the other costly aspects of crystallization noted above are usually retained.

Another disadvantage of most prior art crystallization processes is that they are not particularly energy-efficient. For example, temperature driving forces for heat exchange are often several tens of degrees. Further, the removal of a solvent such as water from material such as salts and sugar requires substantial energy to be added to the system.

The use of crystallization processes at triple point conditions for desalination of sea water is described in Rudd, Powers, & Sirola, *Process Synthesis*, pp. 259-280 (1973); *Chemical Engineering*, May 7, 1979, pp. 72-82 and *Scientific American*, December 1962, pp. 41-47. These prior art processes include direct contact heat exchange systems with and without the use of a secondary refrigerant. In a single stage system, the use of evaporative cooling to form a solid phase and the melting of the solid phase by direct contact with a compressed evaporation vapor are also described. It is believed that these prior art systems were not found to be entirely satisfactory due in part to their inability to provide economically high production rates. Specifically, the production rates were limited by the contamination of the evaporation vapor with salt due to its entrainment during the extremely agitated conditions of evaporation (or more descriptively, boiling) at high production rates. The contamination problems were resolved through the use of an increased number of lower production rate vessels in the process, but this solution resulted in economically undesirable increases in the capital costs of the process and of substantial abandonment of the process.

By way of summary, all of the prior acid gas removal processes have had a number of serious disadvantages involving troublesome problems and/or excessive capital costs and/or operating costs. Further, the use of known crystallization processes in such acid gas removal processes would give rise to similar disadvantages particularly associated with prior crystallization processes.

SUMMARY OF THE INVENTION

In accordance with the present invention, all of the aforementioned relatively high boiling point contaminants may be selectively and substantially completely removed from gas mixtures containing lower boiling components of primary value, and a highly purified end product may be produced at greatly reduced capital and operating costs. For convenience in describing and defining the present invention, normal boiling or sublimination temperatures (at one atmosphere absolute pressure) colder than $-86°$ C. are considered to be relatively low, and normal boiling point or sublimination temperatures warmer than $-86°$ C. are considered to be relatively high.

The process of the present invention is more nearly reversible and requires a lesser net energy input than prior processes; absorbent losses are inherently replaced in the process or are minimal; relatively low viscosity absorbents are used, with improved stage efficiency and savings in pumping costs; the removal of heat of absorption is facilitated by phase changes in the absorbents, which minimizes heat exchange costs; no objectionable environmental pollution is caused; the separated carbon dioxide can be recovered in a pure condition if desired, the separated hydrogen sulfide is recoverable in a desirably high concentration for processing in a Claus plant; corrosion problems are minimal; and a residual primary gas product is recovered that is low in carbon dioxide content and is essentially free of sulfur-containing molecules, including carbonyl sulfide. Further, the novel and preferred crystallization process disclosed herein minimizes heat exchange surfaces, completely avoids the freezing of crystals on cooling surfaces, and uses substantially only direct heat transfer for forming and melting the crystals. This crystallization process also eliminates mechanical conveyance of crystals. In both a single stage application of the process and a cascaded arrangement with a number of stages, it is not necessary to transport solids substantially free of liquid within the stage or between stages; only liquid, gas, or solid-liquid slurries are transported within or between stages, with the majority of transported streams being liquid or gas and the transportation of solid-liquid slurries being eliminated in some instances. This novel crystallization process is also more energy-efficient than most prior art processes, since the temperature driving forces for heat exchange are minimized through the use of direct heat transfer techniques.

Although the different procedures utilized for removing sulfur-containing gases and for removing carbon dioxide from gas mixtures may be practiced separately in accordance with the present invention, their integration into a single process as herein disclosed provides practical and economic advantages.

For removing hydrogen sulfide, carbonyl sulfide, and additional impurities other than carbon dioxide from a gas containing carbon dioxide, a pressurized stream of the gases to be treated is first completely dehydrated. Tars and other very high boiling impurities are condensed and removed with the water in this step. The dehydrated gas stream is then cooled to a temperature as close as possible to its dew point temperature (the temperature at which a liquid phase rich in carbon dioxide begins to condense) at the process pressure.

The dehydrated and still pressurized gas stream at substantially the dew point temperature mentioned above is then contacted by a countercurrent stream of a liquid carbon dioxide refrigerant-absorbent in one or a succession of absorption columns. Hydrogen sulfide, carbonyl sulfide, other sulfur-containing molecules, and other relatively high boiling point molecules are essentially completely absorbed by and removed with the residual liquid carbon dioxide absorbent, the heat of absorption being dissipated as heat of vaporization of a portion of the absorbent. The partially purified residual gas stream emerges from this section of the system at substantially the pressure and temperature at which it entered and with a somewhat increased content of carbon dioxide constituting the only significant impurity still to be removed therefrom.

The residual liquid carbon dioxide absorbent and the absorbed relatively high boiling point gases withdrawn from the absorption column or columns are stripped of any small amounts of valuable low boiling point gases unavoidably entrained therewith, the latter gases being recycled within the process. The stripped mixture of still liquid carbon dioxide absorbent and absorbed impurities (generally sulfur-containing gases) is then processed to separate at least a part of the carbon dioxide and (as hereinafter described) to recover pressure energy and refrigeration potential as economics may dictate. This separation may be accomplished by fractional distillation, crystallization by freezing, extractive distillation, or other means, while producing substantially pure carbon dioxide, which may be reused as absorbent or may be removed as by-product. Exemplary, more or less conventional, distillation and low temperature crystallization processes are disclosed herein for alternative use, or for conjoint use, to separate a relatively pure liquid carbon dioxide from the residual mixture of carbon dioxide absorbent and impurities absorbed thereby, the choice being dictated primarily by the operating pressure of the acid gas separation process with which they are associated. Also disclosed herein, as a replacement for both of such more or less conventional systems for recovering high purity liquid carbon dioxide from that residual mixture, is a novel, greatly improved, and presently preferred, low temperature crystallization process.

The novel crystallization process is not only useful in the acid gas separation process of this application, but, as indicated above, also has broad utility for recovering many different materials that are separable by freezing them out of admixtures with other materials. For example, in sharp contrast with the prior art desalination efforts, the novel crystallization process may be cascaded in series to substantially eliminate the prior art contamination problems resulting from entrainment of salt in evaporation vapor at desirably high production rates. In fact, as distinguished from desalination wherein the salt impurity has no significant vapor pressure and entrainment is the basis of contamination, the novel crystallization process through the use of series connected stages enables the separation of an excluded material or impurity having an appreciable vapor pressure which causes the material to be present as a component of the evaporation vapor. Further, the presence of the excluded material in the evaporation vapor is used to effect, in whole or in part, the flow of the excluded material through the process for purposes of separation from the crystallizable material.

Whatever process or processes may be used to recover a high purity liquid carbon dioxide from the residual liquid carbon dioxide absorbent and impurities absorbed thereby, the thus concentrated mixture of impurities consists largely of sulfur-containing gases and residual carbon dioxide. This mixture may be further processed for the recovery of sulfur, for example, in a Claus plant, or it may be otherwise disposed of.

After the removal of sulfur-containing gases and other impurities from the main gas stream, as described above, the still pressurized, residual, main gas stream is further cooled to near the triple point temperature of carbon dioxide to prepare it for a final carbon dioxide absorption operation. Depending upon the main gas stream operating pressure, a considerable amount of carbon dioxide may be condensed and separated in the course of such cooling (more at high operating pressures). This cooling of the main gas stream is suitably performed by passing it through a series of indirect heat exchangers. The heat exchange medium used to effect such cooling may be any or a combination of several low temperature fluid streams produced in the process. The carbon dioxide condensed in this manner is withdrawn as a liquid stream at substantially the initial gas stream pressure and may provide some or all of the absorbent required in the first absorption step described above, any required make-up being supplied as also mentioned above.

The residual, further purified gas stream is discharged from that series of indirect heat exchangers at approximately its initial pressure, but at about $-55°$ C., and flows to the abovementioned, final, carbon dioxide absorption operation. In that final operation, the main gas stream is first brought into intimate contact with an absorbent that comprises a particulate solid having a high heat absorption capability and that is below the triple point temperature of carbon dioxide (i.e., colder than $-56.6°$ C.). Under these conditions, most of the remaining carbon dioxide content of the gas stream is condensed or frozen, removed with the absorbent, and vaporized or sublimed therefrom.

According to the presently preferred manner of practicing this invention, the particulate solid of the absorbent for this final carbon dioxide removal operation is suspended in a liquid vehicle as a pumpable slurry. In this case, the gas stream and absorbent slurry are brought into intimate contact by counter-current flow through a conventional absorption column or series of columns.

The presently preferred absorbent for use at this point in the process is a partially frozen mixture of carbon dioxide and a liquid or liquids having low viscosity, low vapor pressure, high solubility for carbon dioxide, relatively low solubility for lower boiling point gases, low reactivity, good stability, and, in the mixture, a range of freezing points below $-56.6°$ C. Examples of such liquids are: ethers, such as di-n-ethyl ether, di-n-propyl ether, di-n-butyl ether, and t-butyl methyl ether; ketones, such as methyl ethyl ketone, 2-pentanone (methyl propyl ketone), t-butyl methyl ketone, and methyl isobutyl ketone; methanol, hydrocarbons, such as heptane and hexane; aldehydes, such as butanal, pentanal, and 2-methyl butanal; and inorganic liquids, such as fluorosulfonic acid. The solid phase of the mixture is suspended in the liquid phase as a pumpable slurry, preferably provided at a temperature of about $-70°$ to $-75°$ C. as it begins its flow through the absorption column or columns. When such an absorbent slurry contacts the gas mixture stream still containing an appreciable amount of gaseous carbon dioxide, simultaneous direct heat transfer and mass transfer occur between the gas, liquid, and solid phases. Gaseous carbon dioxide of the gas stream condenses and, by solution or entrainment, becomes part of the liquid phase of the absorbent, and the solid phase of the absorbent concurrently melts in absorbing the heat of condensation and solution of the carbon dioxide. Thus, carbon dioxide of the gas mixture stream is transferred from the gas to the liquid phase while the solid phase of the absorbent slurry liquefies, and both augment the liquid phase of the absorbent.

The term "refrigerant-absorbent" is used hereinafter to characterize both the first-described liquid carbon dioxide absorbent for relatively high boiling point gases and the last-described slurry absorbent for gaseous carbon dioxide. As so used, the term "refrigerant-absorbent" refers to an absorbent that, in whole or in part, undergoes a change of phase during the absorption process, the change of phase enabling it to utilize at least a portion of the heat of absorption to effect its own partial or complete phase change. Such an absorbent is to be distinguished from one that depends solely on its specific heat for its heat absorbing capability, without undergoing a phase change.

As part of the presently preferred form of the final carbon dioxide absorption operation, the gas mixture stream, still at substantially the same operating pressure, is finally contacted with only the liquid phase of the preferred refrigerant-absorbent slurry that has been processed to have a low content of dissolved carbon dioxide, as hereinafter described in more detail. This final step can dissolve and remove carbon dioxide to almost any desired degree without further temperature reduction. As a result, a finally purified gas mixture may be withdrawn from one end of the final absorption column or columns at near the initial operating pressure of the system and at a temperature of about $-70°$ C. to $-75°$ C. The final liquid absorbent and carbon dioxide dissolved therein continue to move downwardly so as to merge with and augment the liquid phase of the refrigerant-absorbent slurry.

The thus-combined final liquid absorbent and completely melted refrigerant-absorbent, together with the carbon dioxide absorbed thereby, are withdrawn as a liquid stream from the opposite end of the column or columns at a temperature of around $-56°$ C. Any relatively low molecular weight components of the gas mixture being treated that were unavoidably also dissolved or absorbed thereby may be recovered therefrom by stripping them from the combined absorbents and absorbed carbon dioxide and may be added to the final, purified gas stream product after recovering refrigeration potential from both.

Regeneration of the refrigerant-absorbent slurry for recycling is readily effected by reducing the pressure of the liquid stream of combined absorbents and condensed carbon dioxide entrained therewith so that the absorbed carbon dioxide is evolved therefrom and the absorbent liquid mixture is thereby cooled to about $-70°$ C. to $-75°$ C., thus regenerating the solid phase thereof by freezing. The evolved carbon dioxide gas is a substantially pure byproduct.

After regeneration of the refrigerant-absorbent slurry, a portion of the liquid phase thereof may be separated therefrom by decantation, warmed, and fed into a gas-liquid separator to facilitate depleting it of most of the remaining carbon dioxide therein. This liquid is then recooled to about $-73°$ C. and pressurized to the main gas stream operating pressure for use as a final liquid absorbent for carbon dioxide to complete the gas purification process.

In order for a liquid carbon dioxide refrigerant-absorbent to exist in contact with the gas stream being treated by the first absorption procedure described above for removing relatively high boiling point impurities, the absorbent preferably should be warm enough to ensure that no solid phase can form. Since the absorbent is predominantly carbon dioxide, which has a triple point temperature of $-56.6°$ C., temperatures warmer than $-56.6°$ C. are operational. Gases dissolved in the liquid carbon dioxide can depress the freezing point by several degrees, so that temperatures somewhat colder than $-56.6°$ C. may also be operational.

An upper temperature limit for the required coexistence of liquid and gas phases in the first absorption procedure described above is the critical temperature of the system. Since the critical temperature varies with the composition, an upper limit is the highest value among the critical temperatures of the pure components of the system. Of the major components present in the main gas stream leaving this absorption system, carbon dioxide usually has the highest critical temperature, $31°$ C. Hence, the theoretical upper temperature limit in the absorption zone for any such system is $31°$ C.

The lowest pressure at which liquid carbon dioxide can be used as an absorbent depends upon the composition of the gas being treated. The pressure must be sufficient for carbon dioxide in the gas and liquid phases to coexist in equilibrium. If the gas is pure carbon dioxide, the lowest operational pressure is about 80 psia, which is the lowest pressure at which pure liquid carbon dioxide can exist. As the fraction of the carbon dioxide in the gas is reduced, the minimum operational pressure rises. At 50% carbon dioxide and where the remaining gas components are low boiling, the minimum operational pressure is about 160 psia. Since gas streams requiring treatment by this procedure necessarily also contain other high boiling point impurities along with the gaseous components to be purified, with the latter generally constituting more than half the total, the carbon dioxide concentration in the main gas stream at this point in the process will generally be less than 50%. Therefore, for the purpose of removing relatively high boiling point impurities, the required gas stream pressure will usually exceed 160 psia and be progressively higher with lower and lower carbon dioxide concentrations in the gas stream.

Theoretically, the limiting maximum gas stream pressure is the highest pressure at which the various liquid and gas phases can exist in equilibrium and is many thousand psia, although varying widely with the compositions involved. Such extremely high pressure would be well above any economically practical operating pressure for most gas purification purposes, but might be used for special purposes. Thus, it is not possible to designate any meaningful, maximum, main gas stream operating pressure.

As will become apparent from the ensuing description of the invention, the temperature to which the crude gases must be cooled for removing sulfur-containing molecules varies directly with the main gas stream pressure at which the raw shift gas is to be processed for that purpose. Also, the proportion of the carbon dioxide that can be removed by simple condensation in heat exchangers at temperatures above the triple point temperature of carbon dioxide increases markedly as the main gas stream operating pressure is increased. As a result, both capital and energy costs for carrying out the overall process of the invention are reduced as the main gas stream pressure is increased up to pressures at least as high as 1000 psia. Obviously, however, pressures can be reached at which such a trend in capital costs may no longer hold true. On the other hand, particular applications of the invention may warrant the use of much higher or lower pressures. Although it is not essential that the main gas stream pressure be maintained at the same level in the successive impurity removing operations of the complete process, practical and economic considerations will generally dictate maintaining a uniform main gas stream pressure throughout those operations.

The ability of a refrigerant-absorbent to utilize the heat of absorption to effect its own partial or complete phase change eliminates or reduces the need for supplying additional refrigeration to the absorption zone. When employing liquid carbon dioxide as an absorbent for relatively high boiling point gases in the manner first described above, substantially all of the heat of absorption is utilized in vaporizing a portion of the liquid absorbent so that no additional refrigeration is required in the absorption zone for maintaining a substantially constant temperature throughout that zone. When using an absorbent slurry of a particulate solid that melts during the absorption process in the manner described above, a large part of the heat of absorption is utilized in melting the particulate solid, thus greatly reducing the amount of additional refrigeration required in the absorption zone to maintain a desirable temperature gradient through that zone.

Alternatively, as hereinafter described in more detail, the particulate solid of the absorbent used for a final carbon dioxide removal operation may be any of a variety of particulate solid materials that are sufficiently resistant to abrasion to retain their particulate solid form and that have a high specific heat for condensing significant amounts of carbon dioxide without requiring excessively frequent regeneration by recooling. Well known techniques for the handling of such particulate solids in fluidized bed operations may be employed for continuously removing particulate solids as they become coated with frozen carbon dioxide, subliming the frozen carbon dioxide therefrom, and recooling and recycling the particulate solid absorbent.

As will be apparent from the foregoing and from the ensuing detailed description of the invention, the portion of the process of the invention by which hydrogen sulfide, other sulfur-containing gases, and other gases having higher boiling points than carbon dioxide are removed from the gas mixture being treated may be used, alone, for separating such high boiling components from relatively low boiling point gases and carbon dioxide.

The successive operations of the invention for separating carbon dioxide may also be used individually or in combination for that purpose when treating gas mixtures that are essentially free of still higher boiling point components such as sulfur-containing compounds. For example, if the gas to be treated is 50% carbon dioxide and its operating pressure is 1000 psia, then the preliminary removal of carbon dioxide by condensation at temperatures above its triple point temperature will reduce the carbon dioxide content of the gas from the initial 50% to about 15%. The final carbon dioxide absorption operation can then be used to remove as much of the remaining carbon dioxide as is desired. On the other hand, if the gas to be treated is only 30% carbon dioxide, and the pressure is only 100 psia, the preliminary removal of carbon dioxide by condensation at temperatures above its triple point temperature is not applicable, but the final carbon dioxide absorption operation can still be used to remove as much of the carbon dioxide as desired.

BRIEF DESCRIPTION OF THE DRAWINGS

In the accompanying drawings

FIG. 6 is a diagrammatic illustration in vertical section of a crystallizer-washer-melter unit used in a single stage separation process.

FIG. 7 is a diagrammatic illustration in vertical section of a washer-melter unit used in a single stage separation process.

DETAILED DESCRIPTION OF THE INVENTION

The invention will now be described in more detail, with particular reference to the removal of acid gases from the raw "shift gases" produced by coal gasification (as distinguished from coal liquefaction). As is well understood in that art, such processes and the composition of their gaseous end products may be varied according to the particular coal being processed, the degree of gasification sought, and the contemplated end uses for the gas product, as well as economic and environmental considerations. The raw shift gases are commonly discharged from such processes at elevated temperatures and pressures which vary from process to process.

For illustrative purposes, the composition of the raw shift gases to be treated by the process of this invention will be assumed to comprise the following typical components and proportions:

| Component | Mol Fraction |
|---|---|
| $H_2$ | 0.4068 |
| CO | 0.1356 |
| $N_2$ | 0.0052 |
| $CH_4$ | 0.1218 |
| $CO_2$ | 0.3189 |
| $H_2S$ | 0.0111 |
| $H_2O$ | 0.0005 |
| COS | 0.0001 |
| HCN | Trace |
| $NH_3$ | Trace |

The exemplary processing of such a gas mixture will be described on the further assumption that the mixture is received from a coal gasification plant at 25° C. and 1000 psia and is processed at that pressure. How the process and apparatus are desirably altered for processing such a gas mixture at a substantially lower pressure of about 300 psia will be explained in the course of that description.

Figure 1:
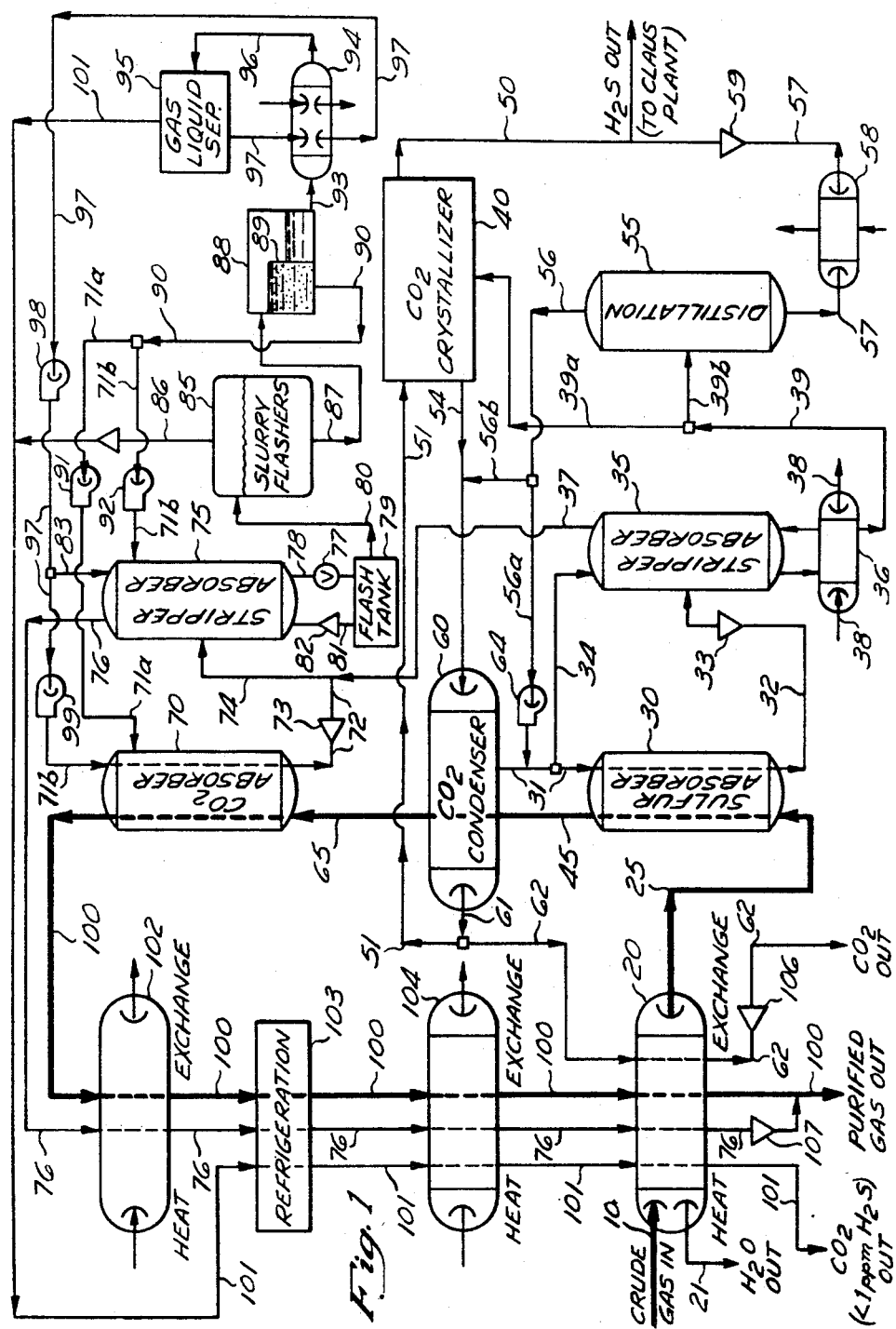
FIG. 1 is a general flow diagram for a system in which the four successive gas treatment operations of the invention are integrated for primarily removing, respectively, water, hydrogen sulfide, and other sulfur-containing gases, a part of the carbon dioxide, and, finally, most of the residual carbon dioxide (down to a fraction of 1 mol percent if desired) from a gas mixture being treated.

Referring now to FIG. 1 of the accompanying drawings, the raw shift gas mixture of the foregoing composition is introduced into the illustrated purification system through a line 10 as a continuously flowing stream at a temperature of about 25° C. and a pressure of 1000 psia. From the line 10, the gas mixture stream flows, first, through a heat exchange system 20 for dehydrating the stream and precooling it to its dew point temperature, that temperature in this example being about −27° C. The dehydrated stream then flows via a line 25 through a sulfur absorption system 30 for removal of its content of relatively high boiling point components, particularly hydrogen sulfide and other sulfur containing molecules. The residual, partially purified stream then flows via a line 45 through another heat exchange system 60 for further cooling it to condense and remove the bulk of its content of carbon dioxide and to discharge the residual stream at a temperature of about −55° C., only slightly warmer than the triple point temperature of carbon dioxide. The residual, partially purified stream then flows via a line 65 through a final carbon dioxide absorption system 70 for the removal of additional carbon dioxide while further lowering the main gas stream temperature to well below the triple point temperature of carbon dioxide. The final, residual, purified gas stream emerges from the final absorption system 70 via a line 100 at near the initial 1000 psia pressure of the raw shift gases and at a temperature of about −73° C. Before being discharged as the finally purified product, this gas stream in the line 100 is routed through another heat exchanger 102, then through a refrigeration unit 103 for recooling and, thence, back through additional heat exchangers for utilizing its refrigeration potential in the process.

The main gas flow to and through the several successive purification and heat exchange steps just described is emphasized in the drawing by heavy solid and dotted lines. Those several gas purification and heat exchange steps of the process and their interdependency in the presently preferred overall system will now be described in detail.

Precooling and Dehydration

The precooling and dehydration system 20 may comprise a series of indirect heat exchangers of conventional design (only one being shown) for progressively cooling the raw shift gases entering this system via the line 10 to substantially the dew point temperature of the particular gas mixture, in this case about −27° C. Such cooling condenses substantially all of the water content of the main gas stream entering the process through the line 10. The condensed water is removed via a condensate line 21 leading to a waste water clean-up system (not shown), which should be selected according to the nature and quantity of the impurities necessarily condensed and removed with the water. As indicated in the drawing and explained below, the finally purified gas stream and three other gas product streams of different temperatures may be used as the cooling media in these heat exchangers The precooling and dehydration system 20 will also include a final dehydration step (not shown) before cooling below 0° C. for removing the last traces of water from the main gas stream. Conventional water scavenging steps, such as those employing molecular sieves, activated alumina absorbents, etc., may be used for this purpose.

The precooled and dehydrated main gas stream flows from the system 20 via the line 25 to the absorption system 30 at near the initial gas stream pressure of 1000 psia.

Removal of Sulfur-Containing Gases

The absorption system 30 for removing relatively high boiling gases, particularly hydrogen sulfide and other sulfur-containing gases, from the dehydrated main gas stream, will suitably comprise a multistage series of sieve tray absorption columns of conventional design. In each absorption column of such a system, the main gas stream moves upwardly, countercurrent to and in intimate contact with a downward flow of liquid carbon dioxide absorbent supplied by a line 31 at 1000 psia and at the main gas stream temperature of about −27° C.

During travel of the main gas stream through the absorption system 30, substantially all of the hydrogen sulfide and other sulfur-containing molecules, along with such other relatively high boiling point molecules as may be present, are absorbed and removed from the main gas stream by the liquid carbon dioxide absorbent. At the temperature and pressure prevailing in this system, the heat of absorption of the absorbed gases is utilized in vaporizing some of the liquid carbon dioxide absorbent so that the liquid carbon dioxide functions as a refrigerant-absorbent. This causes a small net increase in the amount of gaseous carbon dioxide in the main gas stream at the expense of liquid carbon dioxide absorbent and permits the absorption to occur with negligible increase in temperature of the gas stream or of the absorbent.

The liquid carbon dioxide absorbent and absorbed hydrogen sulfide and other heavier molecules are withdrawn from the absorption system 30 at the pressure and temperature maintained therein (about 1000 psia and −27° C.) via a line 32, are passed through an expander 33, by which their pressure is lowered to around 125 psia, and are discharged into a stripper-absorber column 35 equipped with a reboiler 36.

In the stripper-absorber 35, the lighter molecules (hydrogen, carbon monoxide, nitrogen, and methane) that are also absorbed in small amount by the liquid carbon dioxide absorbent in the absorption system 30 are stripped from the still liquid absorbent and other absorbed gases. A relatively small amount of the fresh liquid carbon dioxide absorbent flowing in the line 31 is introduced into the upper end of the column 35 through a branch line 34 for countercurrent contact with the upwardly moving light fractions in the upper end of the column 35 for absorbing any traces of sulfur-containing molecules entrained with the light fractions. By using this supplemental absorption procedure in the column 35, the stripped light fractions and some gaseous carbon dioxide may be withdrawn from the upper end of the column 35 essentially free of sulfur-containing molecules and be moved through a line 37 for further processing, as hereinafter described.

The reboiler 36 requires only a small amount of heat that may be supplied in any convenient manner, as by moving any available heating fluid therethrough via a line 38. The reboiler discharge via a line 39 consists essentially of liquid carbon dioxide absorbent and absorbed sulfur-containing molecules in a total concentration therein of about 4 mol percent. This stream is processed further to increase its concentration of sulfur-containing molecules to about 25 mol percent or more, as desired to produce an economical feed stock for a Claus plant for recovering the sulfur in elemental form. The use of the novel crystallization process for this purpose is subsequently described in detail, but the production of an economical feed stock for a Claus plant using more conventional procedures is immediately described herein. To that end, the desired Claus plant feed stock concentration may be produced by separating carbon dioxide by distillation, crystallization, or a combination of distillation and crystallization as hereinafter described. Distillation can be quite effective for producing a carbon dioxide distillate having the requisite purity for reuse as absorbent in the sulfur absorber 30 and in the stripper-absorber 35, but will generally be more costly and, therefore, is desirably avoided. It is economically feasible to use a combination of distillation and crystallization, with a major portion of the separation being done by crystallization and a lesser portion being done by distillation in order to minimize the distillation requirements and proportion of the total separation costs derived from the more costly distillation technique.

At high main gas stream pressures of around 2000 psia, sulfur-free carbon dioxide may be condensed in the condenser system 60 in ample amount to satisfy the above-described liquid carbon dioxide absorbent needs of the process in both the absorption system 30 and the stripper absorber column 35. Therefore, when processing a main gas stream at such a high pressure, all of the stream flowing in the line 39 may be passed through a branch line 39a to a carbon dioxide crystallizing system 40.

At lower main gas stream pressures, less carbon dioxide can be condensed in the condenser system 60 for transmittal through the line 31 to the sulfur absorber 30 and through the line 34 to the stripper-absorber 35, in which case makeup carbon dioxide absorbent is required from another source. For this purpose, a part of the stream flowing in the line 39 is passed through a branch line 39b to a distillation system 55, described further below, and a liquefied, substantially pure carbon dioxide distillate produced in the distillation system supplies the makeup liquid carbon dioxide absorbent. When the main gas stream pressure is below about 250 psia, all of the flow through the line 39 may be to the distillation system 55 for maximizing the amount of substantially pure carbon dioxide produced therein for use as absorbent, and the crystallizer 40 may be idle.

Thus, in a plant designed solely for operation at a main gas stream pressure of about 2000 psia, the distillation system 55 may be omitted, and in a plant designed solely for operation at a main gas stream pressure below about 250 psia, the crystallizer 40 may be omitted. For a plant operating at intermediate main gas stream pressures, both the crystallizer and distillation system may be employed, each being tailored, of course, to process the desired flow therethrough.

Figure 2A:
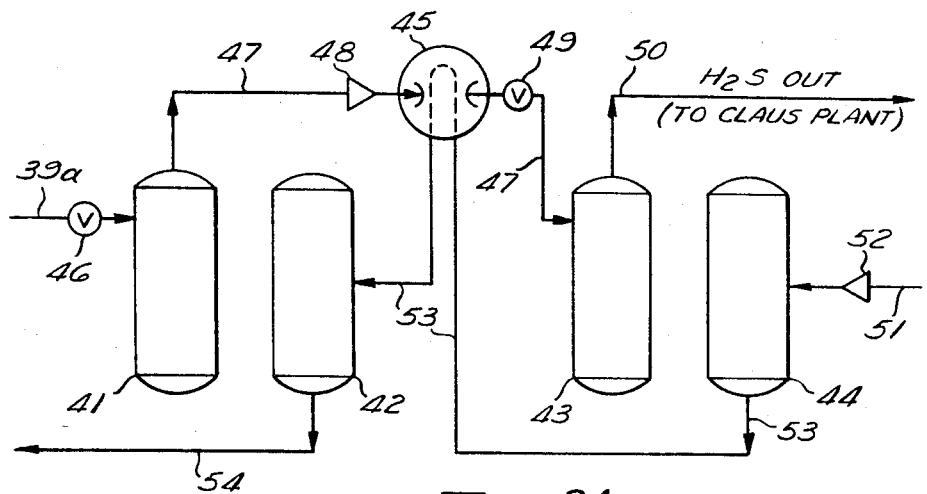
FIGS. 2A and 2B are general flow diagrams showing in more detail a relatively simple carbon dioxide crystallizer (indicated only generally in FIG. 1) in its two alternating conditions of operation.
Figure 2B:
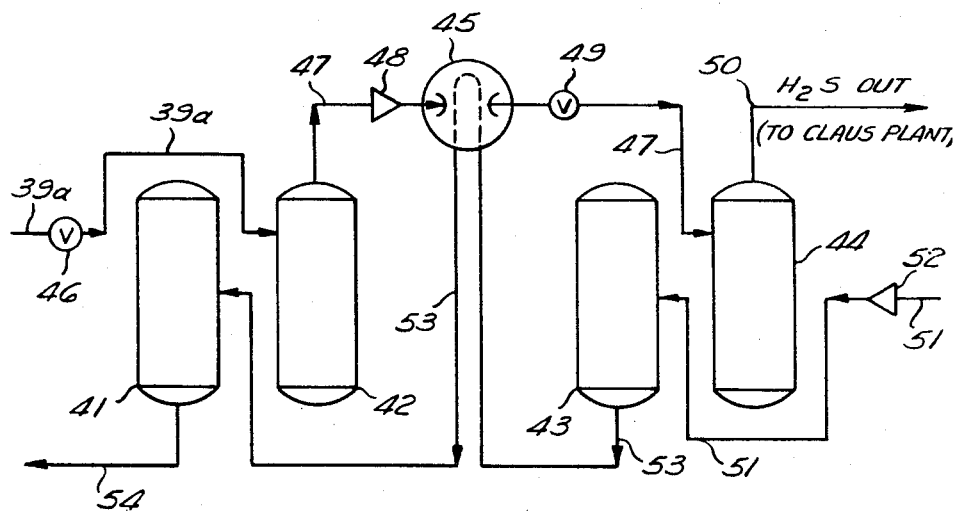

Referring now to the carbon dioxide crystallizer 40 as shown in FIGS. 2A and 2B, it may suitably comprise four tanks 41, 42, 43, and 44. During one period of a two-period operating cycle, the tanks 41 and 43 are connected in series with one side of an intervening heat exchanger 45 for performing a two-stage process of forming and depositing solid carbon dioxide in each tank 41 and 43. The other two tanks 42 and 44 are connected in series with the other side of the intervening heat exchanger 45 for performing a two-stage process of melting and discharging as a liquid the solid carbon dioxide formed and deposited in these two tanks during the preceding period of the operating cycle. FIG. 2A shows that relationship. At the conclusion of the first-described period, the tank interconnections are switched by appropriate valving so that, during the other period of the cycle, carbon dioxide is formed and deposited in tanks 42 and 44 by the same two-stage process as before while carbon dioxide is melted and discharged from the tanks 43 and 41 by the same two-stage process as before. FIG. 2B shows the latter relationship.

Considering FIG. 2A in more detail, the liquid carbon dioxide absorbent and absorbed sulfur containing molecules flowing from the line 39 (see FIG. 1) into the branch line 39a pass through a valve 46 for feeding them as a spray into the tank 41, which is maintained at a pressure of about 60 psia (well below the 75.1 psia triple point pressure of carbon dioxide). To enhance atomization, the pressure of the liquid in the line 39a is desirably increased to around 200 psia by a pump (not shown). Under these conditions, part of the liquid carbon dioxide flashes into solid carbon dioxide that accumulates in the tank 41, and a gas mixture of carbon dioxide and sulfur-containing molecules is formed therein and withdrawn overhead via a line 47 at the required rate for maintaining the tank pressure near the desired 60 psia. A pressure relief valve (not shown) in the line 47 may be used to effect the required pressure control. This gas mixture is then compressed to about 85 psia by a suitable compressor 48 or the like in the line 47, is liquefied by indirect heat exchange in the heat exchanger 45 in the line 47, is pressurized to around 200 psia by a pump (not shown), and, as regulated by a valve 49, is sprayed into the tank 43 maintained at a pressure of about 18 psia. Additional carbon dioxide crystals are thus formed and accumulated in the tank 43, and a residual gas mixture of carbon dioxide and sulfur-containing molecules is again withdrawn overhead, this time via a line 50 (see FIG. 1) for flow to a Claus plant. By the two-stage removal of carbon dioxide as described, the final residual gas mixture taken off through the line 50 may be concentrated in sulfur-containing molecules to the 25 mol percent or so desired for an economical Claus plant feed.

During the above-described formation and accumulation of solid carbon dioxide in the tanks 41 and 43, solid carbon dioxide similarly accumulated in the tanks 42 and 44 during the preceding half cycle is melted and removed. For this purpose, gaseous carbon dioxide introduced to the crystallizer 40 via a line 51 (see FIG. 1) is compressed by a compressor 52 in the line 51 to about 85 psia and is discharged into the tank 44 where it condenses while melting the solid carbon dioxide therein. The resulting liquid carbon dioxide flows via a line 53 through the heat exchanger 45, where it is vaporized before flowing on through an extension of the line 53 into the tank 42. The melting of solid carbon dioxide and the condensing of gaseous carbon dioxide again occur, and the total of the thus-formed liquid carbon dioxide is discharged from the crystallizer 40 through a line 54 (see FIG. 1).

At the conclusion of the two operations in the tanks 41–44 described above, the system is converted by valve changes to the arrangement shown in FIG. 2B. In the same manner, during the next half cycle of operation, solid carbon dioxide is formed and deposited in the tanks 42 and 44 while solid carbon dioxide previously formed in the tanks 41 and 43 is melted therein and is discharged via the line 54.

Liquid carbon dioxide discharged from the crystallizer 40 will have a concentration of sulfur-containing molecules below 250 ppm. Any desired lower concentration of sulfur-containing molecules may be achieved by repeating the crystallization operation. The resulting liquid carbon dioxide is discharged, preferably after its pressure energy and refrigeration potential are recovered as hereinafter described with reference to FIG. 1.

Referring now to the nature of the distillation system 55, shown only diagrammatically in FIG. 1, it should be a multi-stage system including a feed vaporizer and a distillate vapor compressor. The system may be of conventional design for processing the liquid carbon dioxide absorbent and absorbed sulfur-containing gases introduced through the line 39b for separating a portion only of the carbon dioxide in a substantially pure form (about 1 ppm of sulfur-containing molecules) which, with recompression and heat exchange against the incoming liquid feed, may be discharged as a liquid through a line 56. A liquid residue, in which the concentration of sulfur-containing molecules is at or near 25 mol percent, may be withdrawn through a line 57. Depending upon the requirements of the process as determined primarily by the main gas stream pressure, part or all of the liquid carbon dioxide from the line 56 may flow through the line 56a, aided by an interposed pump 64, and into the liquid carbon dioxide absorbent supply line 31 as makeup absorbent, and part or all may flow through the line 56b into the line 54 that provides coolant for the carbon dioxide condenser system 60. The concentrate of sulfur-containing molecules in the residual liquid carbon dioxide vehicle flows in the line 57 through an interposed heat exchanger 58 and expander 59 for recovery of refrigeration potential and pressure energy before merging with the similar material discharged via line 50 from the carbon dioxide crystallizer 60 and flowing therewith to a Claus plant.

The residual main gas stream discharged from the absorption system 30 via the line 45 will have had its original content of hydrogen sulfide and higher boiling point molecules substantially completely removed. By proper absorption column design and with appropriate flow rates, any trace of sulfur-containing compounds in the discharged gas mixture can readily be kept as low as 1 ppm by weight. This leaves only carbon dioxide as an acid gas contaminant still to be removed.

As previously indicated herein, carbonyl sulfide is commonly encountered as a contaminant in very small amounts in gases also contaminated by other sulfur-containing molecules. By reason of its toxicity and its tendency to interfere with various chemical reactions, carbonyl sulfide must generally be removed from gas mixtures in which it is found. As also previously indicated herein, some prior acid gas removal processes are not capable of removing carbonyl sulfide or are capable of doing so only by substantially increasing absorbent flows relative to the flows of the crude gases being purified. By contrast, an advantageous characteristic of the above-described operations for separating sulfur-containing and other relatively high boiling point gases from relatively low boiling point gases is its inherent ability to remove carbonyl sulfide even more effectively than hydrogen sulfide. Stated differently, the foregoing operations inherently separate all of the carbonyl sulfide when performed with the minimum liquid carbon dioxide absorbent flow that is capable of removing all of the hydrogen sulfide, so that no additional cost is entailed for carbonyl sulfide removal.

The ability of the liquid carbon dioxide absorbent to remove carbonyl sulfide even more effectively than hydrogen sulfide is quite surprising since most other physical absorbents absorb hydrogen sulfide more effectively than carbonyl sulfide. This is illustrated by consideration of the gas-liquid solubilities or vapor liquid equilibria. These solubilities or equilibria, as characterized by the constants K, are functions of the liquid and gas composition and either the pressure or temperature, and are represented by the formula:

(1) $K = y/x$ where, y is the mole fraction of soluble component in the gas and x is the mole fraction of soluble component in the liquid absorbent, with equilibrium between the gas and liquid absorbent.

In a countercurrent absorption column, the flow rate of the liquid absorbent approaches a lower limit L, as the number of contacting stages is increased. The relationship between the minimum liquid absorbent flow rate L and the flow rate V of the gas to be processed is expressed as follows:

(2) $L = KV$

Similarly, the minimum liquid absorbent flow rates for purposes of absorbing hydrogen sulfide and carbonyl sulfide may be expressed as follows:

(3) $L_{H2S} = (K_{H2S})V$ (4) $L_{COS} = (K_{COS})V$

Dividing, for purposes of comparison:

$$L_{COS} = \frac{K_{COS}}{K_{H2S}} L_{H2S} \quad (5)$$

Accordingly, the flow of liquid absorbent needed to absorb carbonyl sulfide will be greater or less than the flow needed to absorb hydrogen sulfide, depending on whether $K_{COS}/K_{H2S}$ ("K factor ratio") is greater or less than one.

The K factor ratios for liquid carbon dioxide and the two most widely used physical absorbents for acid gases are reported below for purposes of comparing the flow rates required to absorb carbonyl sulfide when it is to be removed from the gas mixture being processed together with the hydrogen sulfide present. Those commercial absorbents, namely, refrigerated methanol and "Selexol solvent" (the dimethyl ether of polyethylene glycol employed as the absorbent in Allied Chemical Corporation's Selexol process), are believed representative of the available physical absorbents for acid gases and of their COS/$H_2S$ absorption characteristics.

The K factor ratio for liquid carbon dioxide was determined at relatively low concentrations of hydrogen sulfide and carbonyl sulfide, at a pressure of about 100 psia, and at a temperature of about −50° C. The reported K factor ratio for refrigerated methanol, determined at substantially the same conditions, is found in the open literature. The reported K factor ratio for the Selexol solvent is the published Allied Chemical process design value, and it reflects operation at about room temperature, which is normally employed in the Selexol process in view of the high viscosity of the Selexol solvent. These three K factor ratios are set forth in the table immediately below.

| Absorbent | K factor ratio |
|---|---|
| Liquid $CO_2$ | 0.7 |
| Refrigerated methanol | 1.4 |
| Selexol solvent | 4.0 |

The liquid carbon dioxide K factor ratio is less than one and, accordingly, an absorbent flow rate sufficient to absorb all of the hydrogen sulfide present will be more than sufficient to absorb all of the carbonyl sulfide present. In contrast, as determined by its K factor ratio of 1.4, the flow rate of refrigerated methanol required to remove carbonyl sulfide is about 40% greater than that required to remove all of the hydrogen sulfide. Similarly, the Selexol solvent is even less effective in removing carbonyl sulfide, and its flow rate must be increased by about 300% for that purpose.

Accordingly, it is quite unexpected and advantageous that the liquid carbon dioxide absorbent removes carbonyl sulfide even more effectively than it removes hydrogen sulfide. In view of the K factor ratio for refrigerated methanol, it is most surprising that liquid carbon dioxide is effective to remove carbonyl sulfide at flow rates less than 140% of the flow rate required for hydrogen sulfide removal. Thus, the removal of carbonyl sulfide by the liquid carbon dioxide absorbent at flow rates between about 70% and about 140% of the required hydrogen sulfide flow rate is possible. The above conclusions on flow rates of liquid absorbents were reasoned for the limiting case of an infinite number of contacting stages in the absorption column. For a practical number of stages, the economical liquid flow rate of any absorbent is about 1.2 times the minimum liquid absorbent flow rate of the same absorbent. Thus, in practicing the process, the liquid carbon dioxide absorbent flow rate to remove both hydrogen sulfide and carbonyl sulfide may be about 120% of the required minimum flow rate for hydrogen sulfide removal.

In addition to being effective for removing hydrogen sulfide, carbonyl sulfide, and other sulfur-containing gases, liquid carbon dioxide has other properties that contribute to the economy of this part of the overall process. It has an exceptionally low viscosity of about 0.1 to 0.4 centipoise over its range of temperatures in the system, a relatively high specific gravity of about 1.18, and a relatively low molecular weight of only 44. All of these properties contribute to keeping the size and cost of equipment and pumping costs to a minimum. Moreover, liquid carbon dioxide is produced in the process in greater amount than needed as an absorbent so that it imposes no replacement cost but, instead, is produced as a useful byproduct of potential economic value.

Initial Removal of Carbon Dioxide

The partially purified gas mixture stream enters the first carbon dioxide removal system 60 via the line 45 at near the operating pressure of 1000 psia and a temperature of about −27° C. In this system, the gas mixture stream flows through one or a series of indirect heat exchangers of conventional design for lowering the gas mixture stream temperature to about −55° C., which is sufficiently low to condense a major portion of the carbon dioxide content of the stream while also further cooling the stream to near the triple point temperature of carbon dioxide for the purposes of the succeeding, final carbon dioxide removal steps of the process. The resulting liquid carbon dioxide condensate is substantially free of sulfur-containing molecules and supplies a portion of the absorbent requirements of the absorption system 30 and the stripper-absorber 35, to which it flows through the lines 31 and 34. The required additional liquid carbon dioxide absorbent is supplied from the distillation system 55, as described above.

Cooling in the heat exchange system 60 is most suitably performed in a series of indirect heat exchangers (not individually shown). The primary coolant for this purpose may be the liquid carbon dioxide of moderate purity that is discharged from the crystallizer 40 via the line 54, as described above. This liquid carbon dioxide coolant may suitably be recovered from the heat exchange system 60 as a gas at about 75 psia and about −35° C. via a line 61. A portion of the recovered coolant may be recycled back through the crystallizer 40 via the line 51 for melting the solid carbon dioxide formed therein, as described above with reference to FIGS. 2A and 2B. The balance of the coolant recovered from the line 61 may be discharged to the atmosphere via a line 62 after recovering additional refrigeration and pressure energy therefrom, as hereinafter described.

To the extent required, additional refrigeration for the condenser system 60 may be provided by using the final purified gas stream and other product streams of the process as supplemental coolants, as hereinafter described.

When the main gas stream of the present example flows through the condenser system 60 at about 1000 psia, as much as 70% of the carbon dioxide content of the main gas stream may be removed by reducing its temperature to about −55° C., without the use of an absorption agent. As explained above, this is accomplished with relatively simple and inexpensive equipment, using refrigeration potential otherwise generated in the system and conveniently available for that purpose. Thus, the net energy input for this purpose is very small. At lower main gas stream pressures, less carbon dioxide is removed in this manner, as pointed out above, and more must be removed in the succeeding steps of the process.

The main gas stream flows from the condenser system 60 through the line 65 at near its original pressure of 1000 psia and only slightly above the triple point temperature of carbon dioxide. These main gas stream conditions are appropriate for the further and final carbon dioxide removal in the succeeding steps of the process.

Final Carbon Dioxide Removal

The partially purified main gas stream, flowing to the final absorption system 70 via the line 65, is first moved into intimate contact with a refrigerant-absorbent introduced into that system at a temperature well below the triple point temperature of carbon dioxide. In this case, the refrigerant-absorbent advantageously comprises a particulate solid that melts over a temperature range below the triple point temperature of carbon dioxide. Most conveniently, the particulate solid is suspended as a slurry in an appropriate liquid vehicle.

Many different particulate solid materials may be used in the absorption system 70 as the refrigerant-absorbent, or as a part thereof. However, among all of the useful particulate solid materials, a solid frozen from a liquid mixture of carbon dioxide and liquid vehicle is unique, both in its behavior as a refrigerant-absorbent and in its relationship with the liquid vehicle in which it is preferably suspended as a slurry. The composition of that solid may vary from 0% to 100% carbon dioxide, depending upon the choice of liquid vehicle. With 2-pentanone as the liquid vehicle, the solid is pure carbon dioxide. With di-n-propyl ether and di-n-butyl ether, the solid is a mixture rich in carbon dioxide.

Using a solid of the character mentioned above, the liquid vehicle of the refrigerant-absorbent slurry should be a good solvent for carbon dioxide and be miscible with liquid carbon dioxide so as to function as a sink for the liquid produced by progressive melting of the solid phase and absorption from the gas phase as the temperature of the refrigerant-absorbent slurry increases during contact with the main gas stream. Several examples of suitable liquid vehicles are enumerated above herein. Of those mentioned, 2-pentanone is presently preferred, and the following detailed process description applies when using 2-pentanone as the liquid vehicle.

The progressive melting of the particulate solid in the liquid vehicle of the refrigerant-absorbent slurry distributes the cooling effect so that only small temperature and carbon dioxide partial pressure driving forces are required throughout the direct heat transfer-absorption contact between the slurry and the main gas stream. Thus, as pointed out in the foregoing summary of the invention, when such a refrigerant-absorbent slurry contacts a warmer gas mixture stream still containing an appreciable amount of gaseous carbon dioxide, simultaneous direct heat transfer and mass transfer occur between the gas, liquid, and solid phases. Gaseous carbon dioxide of the gas stream condenses, and solid of the refrigerant slurry simultaneously melts, whereby carbon dioxide of the gas mixture stream is transferred from the gas to the liquid phase, solid of the refrigerant-absorbent slurry liquefies, and both augment the liquid phase of the slurry, with the heat of condensation of the gaseous carbon dioxide being absorbed mainly by the melting of solid. Because of these unique relationships and the resulting absorption mechanism, a solid phase frozen from a liquid mixture of carbon dioxide and a liquid vehicle is the presently preferred particulate solid material for the refreigerant-absorbent slurry. The optimum proportioning of solid to liquid in the slurry and the quantity required for treating a given quantity of gas will be determined by the carbon dioxide content of the gas stream being treated, by the specific heats of the several constituents of both the slurry and the gas stream being treated, by the specific temperatures at which the slurry absorbent and the gas stream are introduced into an absorption column or columns for countercurrent flow therethrough, by the absorption column design, and by the ability of pumping equipment employed to move the liquid vehicle and its entrained particulate solids in the system.

The residual, partially purified main gas stream entering the final absorption system 70 from the line 65 at near 1000 psia and about $-55°$ C. may still contain about 13% to 14% carbon dioxide. For treating such a gas mixture with the preferred refrigerant slurry described above, the slurry will suitably contain about 15% by weight of the particulate solid and be at the main gas stream pressure but at a temperature of about $-73°$ C. This slurry is introduced from a line 71a into a sieve tray absorption column of conventional design at a level somewhat below the top of the column (or ahead of the last of a series of such columns) for downward movement countercurrent to an upward flow of the main gas stream. Thus, the uppermost part of the column (or the last one or more of a series of columns) is left available for a final scrubbing of the main gas stream with a carbon dioxide-depleted portion of the liquid phase only of the refrigerant slurry. This final liquid absorbent is introduced through a line 71b for downward movement countercurrent to the upwardly flowing main gas stream before the latter is discharged from the absorption system 70 via the line 100. For this final scrubbing operation, the carbon dioxide-depleted liquid phase absorbent will be at the main gas stream pressure and at a temperature of $-73°$ C. It dissolves the remaining carbon dioxide from the main gas stream down to a final carbon dioxide content of 1 mol percent, or less if desired, depending upon the degree to which the final liquid absorbent was depleted of dissolved carbon dioxide and the severity of the final scrubbing operation. Continuing on down through the column or columns of the absorption system 70, the liquid phase absorbent and dissolved carbon dioxide merge with and augment the slurry absorbent introduced through the line 71a. Both then move together to the bottom of the column (or bottom of the first of a series of columns), absorbing additional carbon dioxide by the phase change mechanism described above.

During contact between the slurry absorbent and the main gas stream, melting of the solid phase of the slurry absorbent preferably proceeds to completion to provide as much cooling as possible for condensing a major portion of the residual carbon dioxide from the gas stream.

Additional refrigeration is required in the absorption system 70 to supplement the in situ refrigeration provided by the refrigerant-absorbent. Such additional refrigeration is provided by indirect heat exchange with the finally purified gas product or with other available cooling fluids as hereinafter explained. It is supplied near the main gas stream inlet end of system 70 where the solid phase of the refrigerant-absorbent is exhausted or is approaching exhaustion. Additional refrigeration is also required adjacent the opposite end of the absorption system 70 in the zone thereof where the main gas stream is finally contacted by the liquid absorbent introduced through the line 71b.

Liquid carbon dioxide formed in the absorption system 70, both by melting and by condensation, is entrained with the liquid vehicle portion of the refrigerant-absorbent and is removed therewith through a line 72 at about −56° C. The finally purified gas stream is withdrawn from this absorption system 70 through the gas product line 100 at about −73° C. and at near the initial main gas stream operating pressure of 1000 psia. The refrigeration potential of the finally purified gas stream in the line 100 is recovered in heat exhangers at various points in the overall system, as mentioned above and further detailed below.

The fully melted, combined absorbent liquids and absorbed carbon dioxide withdrawn from the absorption system 70 through the line 72 at about −56° C. and near 1000 psia are first moved together through a pressure reducer 73 to lower their pressure to about 125 psia for movement via a line 74 into a stripper-absorber 75, along with the light fractions discharged via the line 37 from the prior stripper-absorber 35. This is indicated diagrammatically by the merging of the lines 37 and 72 into the line 74.

In the stripper-absorber 75, the light fractions (hydrogen, carbon monoxide, nitrogen, and methane), that have been unavoidably picked up from the main gas stream during its passage through the absorption system 70 are stripped from the absorbent liquids and absorbed carbon dioxide. The stripped light fractions, unavoidably containing considerable carbon dioxide, are combined with a similar stream 37 from stripper-absorber 35, and the combined gases are treated in the upper part of stripper-absorber 75 to remove most of the carbon dioxide therein, as described more completely hereinafter. From the top of the stripping column 75, the stripped light fractions and only a minor amount of carbon dioxide entrained therewith are withdrawn via a line 76.

The absorbent liquids and most of the absorbed carbon dioxide, at about 125 psia, are withdrawn from the bottom of the stripper-absorber 75 through a valve 77 in a line 78 leading into a flash tank 79, which is maintained at a lower pressure of about 65 psia. This pressure drop results in the flashing off from the liquid of some of the carbon dioxide while the remaining liquid, including all of the absorbent vehicle and most of the carbon dioxide, is withdrawn via a line 80 to a refrigerant-absorbent slurry regenerating system 85. The flashed carbon dioxide gas is withdrawn from the flash tank as it is formed, through a line 81, and, with recompression in a compressor 82, is returned to the bottom of the stripper-absorber 75. There it bubbles upwardly through the liquid therein and assists in stripping the light fractions therefrom. Most of this carbon dioxide gas is then reabsorbed as it rises in the upper part of the stripper-absorber 75 by successively contacting downward flows of the same kind of refrigerant-absorbent slurry used in the absorption system 70 and the same kind of liquid absorbent used therein. These absorbents are respectively introduced into the stripper-absorber 75 via lines 83 and 71b from sources described hereinafter. Thus, the upper part of the stripper-absorber 75 functions similarly to the absorber system 70 in separating carbon dioxide from the stripped light fractions. As a result, the light fractions leaving the stripper-absorber 75 via the line 76 have very little carbon dioxide gas entrained therewith (4 mol percent or less).

The light fractions leaving the stripper-absorber 75 through the line 76 are at a temperature of about −73° C. Accordingly, they are recycled back through the process for recovery of their refrigeration potential before being combined with the purified main gas stream, as described hereinafter.

The liquid effluent from the flash tank 79, flowing to the slurry regenerating system 85 at about 65 psia and about −55° C., has its carbon dioxide content and its temperature progressively reduced by a succession of further pressure reductions in a series of additional flash tanks (not individually shown). The separated carbon dioxide is flashed off as a gas in a high state of purity (less than 1 ppm of sulfur-containing molecules) and is withdrawn via a line 86 at only slightly above ambient pressure and at a temperature of about −75° C. It is then routed back through the process, as hereinafter described, for recovery of its refrigeration potential before it is withdrawn as a useful byproduct or is released to the atmosphere, as economic considerations may dictate. Part of the remainder of the carbon dioxide in the liquid entering the slurry regenerating system 85 remains dissolved in the refrigerant-absorbent vehicle as the latter is progressively cooled by the succession of pressure reductions, and the balance is frozen and physically entrained in the refrigerant-absorbent vehicle as it moves through this system and out through a line 87 as a liquid-solid slurry.

The thus regenerated refrigerant-absorbent slurry flows through the line 87 to a decanting station 88 where a portion of the liquid vehicle of the slurry is separated therefrom, as by flowing over a weir 89 or the like. The remaining regenerated refrigerant-absorbent slurry held back by the weir 89 is withdrawn through a line 90 at slightly above ambient pressure and at a temperature of about −75° C. for recycling to the absorption system 70 and to the stripper-absorber 75. For this purpose, the flow of regenerated refrigerant-absorbent slurry in the line 90 is divided, a major portion flowing from the line 90 into and through the line 71a and through a pump 91 therein for repressurizing the slurry to about 1000 psia as required for it to flow into the absorption system 70 for use therein as previously described. The remainder of that slurry flows into and through the line 71b and through a pump 92 therein for repressurizing the slurry to about 125 psia as required for it to flow into the stripper-absorber 75 for use therein as previously described.

The liquid vehicle of the slurry that is separated at the decanting station 88 is fed via a line 93 through a heat exchanger 94 in which it is warmed as required for evolving most of its dissolved carbon dioxide in a gas-liquid separator 95, to which it flows through a line 96. The substantially pure carbon dioxide evolved in the separator 95 is discharged therefrom slightly above ambient pressure and at a temperature of about −36° C. and is routed back through the process as hereinafter described for recovery of its refrigeration potential before it is withdrawn as a useful byproduct or is released to the atmosphere as economic considerations may dictate.

The vehicle portion of the refrigerant-absorbent slurry that has been separated from the slurry at the decanting station 88 and depleted of dissolved carbon dioxide in the gas-liquid separator 95 is withdrawn from the latter via a line 97 that flows through the heat exchanger 94 where it is recooled by indirect heat exchange with the just separated, cold vehicle portion of the regenerated refrigerant-absorbent slurry flowing from the line 93. Emerging from the heat exchanger 94 through a continuation of the line 97 at about −73° C. and only slightly above ambient pressure, the recooled, carbon dioxide-depleted vehicle portion of the regenerated refrigerant-absorbent slurry passes through a first pump 98 that repressurizes it to about 125 psia before it is divided by diverting a minor portion thereof through the line 83 and into the upper end of the stripper-absorber 75 for use therein as previously described. The major portion of the recooled, carbon dioxide-depleted vehicle portion of the regenerated refrigerant-absorbent slurry continues on through a further extension of the line 97 and through a second pump 99 that further repressurizes it to about 1000 psia before it flows through the line 71b and into the gas discharge end of the absorption system 70 for use therein as previously described.

Although the desired low carbon dioxide content of the finally purified main gas stream emerging from the absorption system 70 could be achieved in the process of the present example by using only the refrigerant-absorbent slurry to absorb carbon dioxide, a slurry temperature of about −96° C. as it enters the absorption system 70 would be required to do so. That, in turn, either would require a greater total pressure drop in the succession of slurry flashers by which the refrigerant-absorbent slurry is regenerated, down to a final pressure below ambient, with obvious disadvantages in terms of capital costs and contamination of the system in the event of leaks, or would require substantially increased capital and operating costs for additional refrigeration. By using the carbon dioxide-depleted liquid vehicle portion of the refrigerant-absorbent slurry as the final absorbent for carbon dioxide, taking advantage of its relatively high capacity for dissolving carbon dioxide even at extremely cold temperatures, the coldest temperature required in the absorption system 70 in the present example is about −73° C., and the above-mentioned disadvantages are avoided.

Recovery of Pressure and Refrigeration Energy

As mentioned above, various product streams from the process are routed back through the system for the recovery of refrigeration potential therefrom. These product streams include the finally purified main gas stream flowing in the line 100, the light fractions withdrawn from the stripper-absorber 75 through the line 76, the high purity carbon dioxide gas withdrawn from the refrigerant slurry regenerating system 85 through the line 86 and from the gas-liquid separator 95 through a line 101, and a portion of the carbon dioxide coolant withdrawn as a gas from the carbon dioxide condenser system 69 through the lines 61 and 62. The first two of those four product streams, in the lines 100 and 76, are at temperatures of about −73° C. and are directly usable in the absorption system 70 as supplemental, indirect heat exchange refrigerants for maintaining the desired temperature gradient therein. For simplicity of illustration, a separate heat exchanger 102 is shown in FIG. 1 of the drawing for recovering refrigeration energy from those two product streams for use in the absorption system 70.

As previously indicated, supplemental cooling for the carbon dioxide condenser system 60 may also be required. The gases flowing out of the heat exchanger 102 through extensions of the lines 76 and 100 may be used for that purpose, along with the gases in the lines 86 and 101, which merge and flow together through an extension of the line 101, as shown. However, all of these last-mentioned streams may require slight recooling or further cooling to provide a sufficient temperature driving force. Therefore, a suitable refrigeration unit 103 may be provided for recooling the gases flowing in the extended lines 76, 100, and 101 before they flow through a supplemental, indirect heat exchanger 104 that may be a part of the heat exchange system 60 but is shown separately in FIG. 1 of the drawing for simplicity of illustration.

The three streams emerging from the supplemental heat exchanger 104 via further extensions of the lines 76, 100, and 101 and the stream emerging from the heat exchanger 60 via the lines 61 and 62 are all at temperatures below −27° C. and may be used as the primary coolants for the incoming crude gas in the heat exchange system 20 mentioned above and shown in the drawing.

As previously explained, the carbon dioxide stream in the line 62 may be depleted of sulfur compounds to any extent desired. It may be discharged to the atmosphere or recovered as a byproduct. Since it is still at a pressure of around 75 psia as it emerges from the heat exchange system 20 in the extended line 62, its pressure energy is recovered in an expansion turbine 106 or the like, as shown, before it is discharged.

The relatively low pressure stream of light fractions flowing through the line 76 from the stripper-absorber 75 should contain not more than 4 mol percent of carbon dioxide and may suitably be combined with the roughly ten times greater quantity of purified gas flowing at high pressure through the line 100. Accordingly, after passing through the heat exchange system 20, the further extended line 76 runs through a compressor 107 and then into the further extended line 100 to provide the maximum, purified, final gas product at close to the initial main gas stream pressure.

The high purity carbon dioxide (less than 1 ppm sulfur compounds) flowing through the further extended line 101 after it emerges from the heat exchange system 20 is at a pressure only slightly above ambient and may be discharged either to a byproduct collection system (not shown) or to the atmosphere as economic considerations may dictate.

In the drawing and descriptions of the heat exchanger 58 for recovering heat from the Claus plant feed discharged from the distillation system 55 via the line 57, no particular source of a heat supplying medium is disclosed. Similarly, in the drawing and description of the heat exchanger 94 for warming the liquid absorbent flowing from the decanting station 88 via the line 93, no particular source of the second of the two heat supplying media indicated in the drawing is disclosed. As in the case of the reboiler 36 associated with the stripper-absorber 35, any suitable, available heat supplying fluid may be used in the heat exchangers 58 and 94, thereby supplying additional cooling wherever needed in the overall system. Obviously, where the temperatures of available heat-supplying fluids are not suitable for their direct use as heat exchange fluids, heat pumps may be employed to effect the needed energy transfer. For example, this expedient may be employed for supplying refrigeration to the final carbon dioxide absorption system 70 near the product gas discharge end thereof, the need for such additional refrigeration being pointed out above.

Throughout the process, wherever significant pressure reductions of sizable fluid streams are required, as described above, expansion turbines driving electric generators may be used to recover the energy released by such pressure reductions and convert it to a form that is conveniently usable in operations that consume energy, as will be apparent to those skilled in the art.

Alternative Carbon Dioxide Absorbents

As previously stated, many different particulate solid materials may be used in the final absorption system 70 as the solid phase of a refrigerant-absorbent slurry employed therein. In the preferred example described above in detail, the solid phase melts as carbon dioxide in the main gas stream is condensed, and both are removed from the absorption zone as a liquid mixture with the refrigerant absorbent vehicle. Instead, the carbon dioxide of the gas stream may be condensed to the solid phase, i.e., frozen, either as a pure compound or in a mixture with material of the absorbent liquid vehicle. In both of these cases, the frozen carbon dioxide is removed from the absorption zone as a solid suspended in the liquid vehicle. In either case, the particulate solid component of such a slurry may be a solid phase of a liquid vehicle consisting of a single compound, or the particulate solid may be suspended in a liquid vehicle of different composition.

Another type of refrigerant-absorbent is a liquid-solid system which has a negligible carbon dioxide content and negligible capacity to dissolve carbon dioxide and other gases. An example is a liquid metal mixture with a freezing range below $-56.6°$ C. Various mixtures of mercury, thallium, and potassium, for example, freeze at temperatures well below $-56.6°$ C. Using such a refrigerant-absorbent system, carbon dioxide of the main gas stream will condense therefrom as a solid for entrainment with the liquid and progressively melting solid phases of such system. Separation of the frozen carbon dioxide from the depleted refrigerant-absorbent slurry and regeneration of the latter are readily accomplished by dropping the pressure of the mixture to below the triple point pressure of carbon dioxide so that the absorbed carbon dioxide sublimes and is separated as a gas. The cooling produced by that sublimation supplies most of the refrigeration required to refreeze the particulate solid material of the refrigerant-absorbent slurry for recycling to the absorber.

Composite materials may be employed as the particulate solid of a refrigerant-absorbent slurry for sorbing carbon dioxide by freezing it out of the main gas stream and adsorbing it onto the surfaces of the composite particles. Thus, one may employ a frozen fluid encased in durable solid walls in the form of small spheres or pellets. The use of such a composite solid refrigerant combines the high heat absorption characteristics of a solid-liquid phase change with the handling characteristcs of permanently solid spheres or pellets. Such spheres or pellets can be made by known technology in many shapes and sizes ranging from microscopic (microencapsulation) to macroscopic (on the order of inches in characteristic dimension). The pellet wall materials may be metal or plastic. The small size composite spheres or pellets of that character can be slurried in a suitable liquid vehicle and used in an absorption column system with only obvious differences in handling procedures and in the character of the process from what has been described above. Such a refrigerant-absorbent slurry may be regenerated while separating the adsorbed carbon dioxide by sublimation by the same regeneration procedure last described above.

However, it is not necessary that such a composite, particulate solid-refrigerant-absorbent for carbon dioxide be suspended in a liquid vehicle as a liquid-solid slurry. Instead, it may be suspended in a gaseous vehicle as a so-called fluidized bed, utilizing well known fluidized bed techniques for continuously removing the composite bodies as they become coated with frozen carbon dioxide, subliming the frozen carbon dioxide therefrom, refreezing the encapsulated refrigerant, and recycling the recooled composite bodies into the fluidized bed. Such composite bodies, including those of larger sizes, may be similarly used in fixed beds, moving beds, ebullating beds, and the like through which the gas stream being treated can be moved to absorb carbon dioxide therefrom.

Other variants of the particulate solid, absorbent or absorbent materials disclosed herein and of the methods for handling them to condense carbon dioxide below its triple point temperature may be employed, as will be recognized by those skilled in the relevant arts.

Alternative Crystallization Process

The novel crystallization process is applicable to systems or mixtures of materials displaying triple point locus conditions as hereinafter discussed more fully and containing a crystallizable material, one or more other materials or impurities which are at least partially excluded from a solid phase containing the crystallizable material obtained from freezing a liquid phase of the system, and an in situ heat transfer material or component. The process is performed at temperatures and pressures such that the gas, liquid, and solid phases of the system coexist nearly in equilibrium. The solid phase is formed and melted at remote locations in a liquid mixture of the materials and, within the liquid mixture, internal, solid and liquid flows are maintained to effect separation of the crystallizable material and the excluded material. The cooling to form the solid phase is provided by evaporation of the in situ heat transfer component, and the heating to melt the solid phase is provided by the condensation or absorption of a vapor phase of the in situ heat transfer component which is introduced into the liquid mixture for direct heat transfer with the solid phase.

The crystallization process may be performed in various cascade process arrangements including a multiple stage, counter-current separation process wherein the solid phase is formed and melted as described above in a plurality of series-connected vessels. In such cascade arrangements, the vapor phase of the in situ heat transfer component for melting the solid phase in a first stage is provided by compressing the evaporation vapor of the in situ heat transfer component from the second stage. Mass flow between stages or vessels is provided by liquid and vapor streams. Thus, a crystallizable material-enriched output obtained upon melting the solid phase in the first stage is passed to the second stage for recrystallization and further purification. An excluded material-enriched output of the second stage is passed to the first stage for further concentration as a liquid reflux stream or as a component of the evaporation vapor of the in situ heat transfer component of the second stage, or both.

As indicated, the evaporation vapor of the in situ heat transfer component provides energy and/or mass flows between series connected stages. Through the use of the liquid reflux stream, the mass flow may be provided independently of the energy flow. This ability to separate the mass and energy flows enables the flow of evaporation vapor to be determined solely by the energy required to melt the amount of solid phase needed to provide a desired production rate of crystallizable material. The flow of excluded material through the reflux stream is used to satisfy any deficiency in the amount of excluded material being conveyed by the evaporation vapor. It is more economical to convey the excluded material as a liquid stream than as a component of a vapor. In the absence of the liquid reflux stream, the flow of excluded material required for the desired production rate would be obtained by increasing the flow of evaporation vapor. This increase in the flow of evaporation vapor will cause additional solid phase to be formed and melted throughout the process, but it will not result in an increase in the amount of crystallizable material product and, therefore, the use of an increased evaporation vapor flow is not a practical alternative means of flow.

The evaporation of the in situ heat transfer component includes boiling thereof which may extend a considerable distance into the liquid mixture. Thus, the term "evaporation" is intended to include boiling herein. As will become more apparent hereinafter, the in situ heat transfer component may comprise a material specifically added to the separation system which undergoes absorption into a liquid phase enriched in the crystallizable material during the melting of the solid or crystal phase to release its heat of absorption. The heat of condensation and the heat of absorption of a given material are substantially the same, and therefore the terms "absorption" and "condensation" can be used interchangeably. For convenience in the further description herein and in the claims, reference to a condensing gas or vapor or vapor phase for purposes of melting the solid or crystal phase in the crystallization process is deemed to also include a gas or vapor or vapor phase undergoing absorption.

Accordingly, the process broadly contemplates a crystallization technique wherein the solid or crystal phase of the system is formed by evaporative cooling of the liquid phase and melted by direct heat transfer with a condensing gas or a gas undergoing absorption. In single stage or plural stage arrangements, the condensing gas may be readily derived from the evaporation of a crystallizable material-enriched liquid phase of the materials which is located remote of the state wherein the solid to be melted is located.

The solid or crystal phase is formed by reducing the pressure below the triple point pressure; liquid cannot persist at pressures below the triple point pressure and, therefore, liquid spontaneously converts to solid and vapor in a ratio determined by the latent heats of fusion and vaporization of the liquid phase. Similarly, the solid or crystal phase is melted by raising the pressure above the triple point pressure in the presence of vapor; solid cannot persist in the presence of vapor at pressures higher than the triple point pressure and, therefore, solid and vapor spontaneously convert to liquid. Again, the ratio of solid melted to vapor condensed is determined by the latent heats of fusion and vaporization. The vapor formed in producing solids below the triple point pressure, and the vapor supplied in melting solids at pressures above the triple point pressure is the in situ heat transfer component. In the purification of carbon dioxide and concentration of the mixture of impurities in the subject acid gas separation process, the solid phase is carbon dioxide, the excluded material is the mixture of impurities, and the in situ heat transfer component is primarily carbon dioxide with a lesser content of the excluded material.

As indicated in the foregoing discussion of the acid gas separation process, the stream flowing in the line 39 from the stripper-absorber 35 consists essentially of liquid carbon dioxide absorbent and absorbed sulfur-containing molecules in a total concentration therein up to about 4 mol percent, which stream may be further processed to produce an economical feed stock for a Claus plant and a high purity liquid carbon dioxide that may be used in whole or in part in the acid gas separation process before being recovered as a by-product or otherwise disposed of. The use of the novel, more sophisticated crystallization process of the present invention for further processing this stream will now be described.

Figure 3:
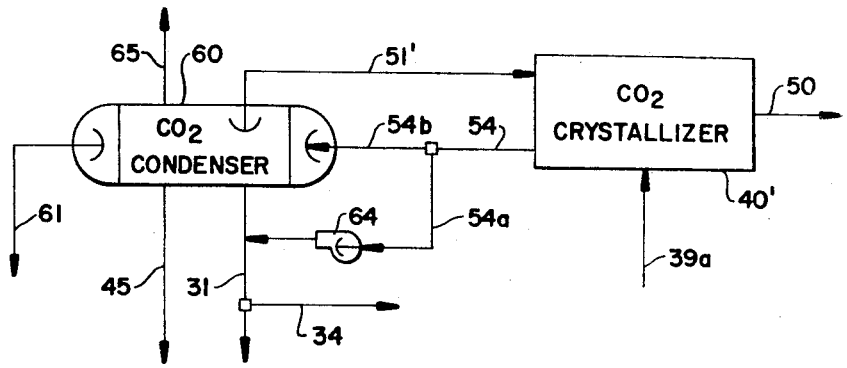
FIG. 3 is a portion of the general flow diagram of FIG. 1 modified to include the novel, more sophisticated crystallizer and crystallization process as a complete replacement for both the distillation system and simple crystallizer in the general flow diagram of FIG. 1.

Referring to FIG. 3, the novel, more sophisticated crystallizer 40' may be directly substituted for the crystallizer 40 in FIG. 1. Alternatively, it may be substituted for both the crystallizer 40 and the distillation system 55 of FIG. 1. In this latter instance, the stream flowing in the line 39, instead of being split between the line 39b to the distillation system 55 and the line 39a to the crystallizer 40, as shown in FIG. 1, is entirely directed through the line 39a of FIG. 1 and, as shown in FIG. 3, flows into the more sophisticated crystallizer 40'. Accordingly, the distillation system 55 of FIG. 1, the branch line 39b leading thereto, and the liquid product lines 56 and 57 (including the heat exchanger 58 and expander 59 interposed in the latter) leading therefrom may be eliminated. Also, as shown in FIG. 3, the purified liquid carbon dioxide product leaving the crystallizer 40' via the line 54 is split between a branch line 54a supplying liquid absorbent to the sulfur absorber 30 and a branch line 54b supplying liquid refrigerant to the carbon dioxide condenser system 60. Further, in order that the gaseous carbon dioxide recycled from the condenser system 60 to the crystallization system 40' be as close as possible to the triple point temperature of carbon dioxide, this recycled carbon dioxide is preferably withdrawn from the condenser system 60 through a line 51' at an intermediate point therein, rather than at the warm end thereof, as shown by line 51 in FIG. 1.

For the illustrated application of the crystallizer 40' to the acid gas separation process, several stages are preferably used to provide a 25 mol percent hydrogen sulfide overhead vapor product to the line 50 feed to a Claus plant and to supply a substantially pure liquid carbon dioxide bottom product back through the lines 54, 54a, and 54b, for further use in the main gas separation process as previously described.

Figure 4:
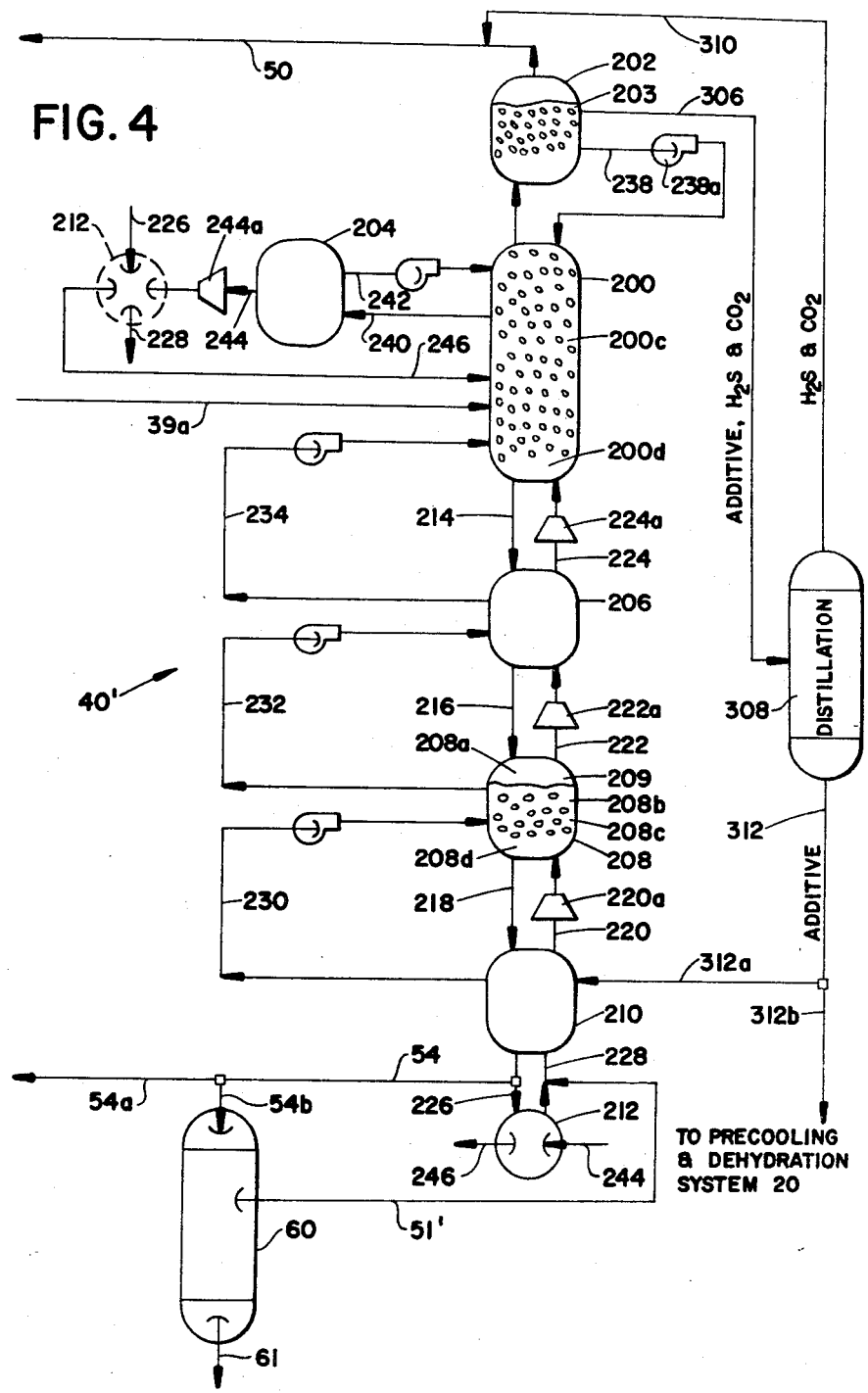
FIG. 4 is a general flow diagram showing in more detail the novel, more sophisticated crystallizer and process.

In contrast with the process in the crystallizer 40, the process in the crystallizer 40', as more fully shown in FIG. 4, is continuous without cycling between crystal forming and melting vessels. The latter crystallization process enables the elimination of the costly distillation system since its effectiveness is not dependent upon the main gas stream pressure, and it is capable of producing liquid carbon dioxide in an amount sufficient for the refrigeration needs of the heat exchanger system 60 and an excess of sufficient purity for use as absorbent in the sulfur absorber 30.

Referring to FIG. 4, the crystallizer 40' includes three series-connected crystallizer-washer-melter vessels, or "CWM's," (206, 208 and 210) as a stripping section to remove hydrogen sulfide and other sulfur-containing molecules from carbon dioxide. The feed is introduced into a washer-melter vessel, or "WM," (200) disposed above the stripping section to provide an upper rectification section for enriching or concentrating the hydrogen sulfide and other sulfur-containing molecules. As shown, it is generally necessary to provide only one stage in the rectification section, since the separation factor upon crystallization is typically so large (on the order of 100 or more) that the crystallizable material-enriched product from a single stage is already substantially purer than the feed.

The number and type of stages shown in FIG. 4 is appropriate for treating the liquid carbon dioxide absorbent and absorbed sulfur-containing molecules (4 mol percent) of the acid gas separation process to provide an overhead product discharged via line 50 containing hydrogen sulfide in a total concentration of about 25 mol percent or more (suitable as feed to a Claus plant) and a substantially pure carbon dioxide bottom product discharged via line 54 and containing less than 1 ppm hydrogen sulfide and other sulfur-containing molecules.

Throughout the cascade of the crystallizer 40', crystalline carbon dioxide is formed and moved in a downward direction and hydrogen sulfide and other sulfur-containing molecules excluded from the crystalline carbon dioxide (referred to herein as "excluded material") is moved in an upward direction. In accordance with the flow directions of the crystallizable and excluded materials, concentration gradients are established throughout the cascade of the crystallizer 40'. Upwardly decreasing temperature and pressure gradients are also established, and there is an upwardly progressing depression of the triple points of the mixtures in the system due to the concentration gradients established therein as hereinafter explained.

The basic processing units in the illustrative crystallizer 40' comprise one WM 200, two associated flashers 202 and 204, and three CWM's 206, 208, and 210. In addition, a heat exchanger 212 is used to provide a condensing vapor to the lower-most CWM 210.

In the stripping section of the crystallizer, liquid streams of progressively purer carbon dioxide are passed downwardly through lines 214, 216, and 218. Vapor streams containing progressively increasing amounts of the excluded material are passed upwardly between the CWM's and WM via lines 220, 222, and 224. Each of the vapor streams is compressed to deliver it as a condensing vapor at the required pressure in the adjacent upper vessel through the use of compressors 220a, 222a, and 224a. In the lowermost CWM 210, a liquid carbon dioxide-enriched stream is withdrawn from the vessel via line 54. A portion of the liquid carbon dioxide flowing in line 54 is passed via branch line 226 th the aid of a pump (not shown) to increase its pressure to heat exchanger 212. The carbon dioxide is vaporized by indirect heat exchange in the exchanger 212 and the vapor phase is returned through line 228 to the CWM 210 to provide a condensing vapor.

In the stripping section, excluded material is also moved in an upward direction by liquid reflux streams of progressively increasing concentration of the excluded material within lines 230, 232, and 234. In each instance, the liquid reflux stream is drawn from a point of highest concentration of the excluded material in a lower CWM and passed to the next higher CWM or WM 200 to augment the liquid phase therein.

A liquid stream having a relatively high concentration of the excluded material is withdrawn from the WM 200 and passed to the flasher 202 via line 236.

Liquid in the flasher 202 is evaporated to provide the excluded material-enriched overhead product which is discharged through the line 50. This crystallizes some carbon dioxide which is returned as a slurry to the WM 200 by means of line 238 with the aid of pump 238a.

The mass flows introduced into the various units of the cascade are preferably introduced at points of matching composition, or as closely matched as possible, in accordance with conventional separation techniques. Generally, the composition of the liquid phase of the introduced material will be matched with the composition of the liquid phase of the material in the unit at the point of introduction.

The opposing liquid and solid flows within the liquid phases in the CWM's and the resulting concentration gradients establish contiguous crystal forming, washing and melting zones in each of the CWM's. This will be better understood by consideration of CWM 208 wherein the liquid, solid, and gas phases are schematically illustrated.

As shown in FIG. 4, a vapor space 208a is provided at the top of the CWM 208 adjacent a free surface 209 of the liquid phase of the materials within the vessel. Evaporation vapor is continuously removed from the vapor space 208a through the line 222, compressed by means of compressor 222a to a pressure substantially the same as that existing in the bottom of the CWM 206, and introduced into the CWM 206 via the continuation of line 222. The continuous removal of vapor from the vapor space 208a provides evaporative cooling of the liquid phase in the CWM 208 and the formation of a solid phase within a crystal forming zone 208b at a pressure and temperature below the prevailing triple point conditions. Under these pressure and temperature operating conditions, liquid present in the crystal forming zone 208b converts to vapor and solid because liquid cannot persist at pressures below the triple point pressure.

The solid phase formed in the crystal forming zone 208b moves downwardly by gravity through an intermediate crystal washing zone 208c to a crystal melting zone 208d provided adjacent the bottom of the CWM 208. As the solid phase moves downwardly through the washing zone 208c, a backwash upward flow of liquid phase from the crystal melting zone 208d washes excluded material from the surface of the solid phase and carries it upwardly toward the crystal forming zone 208b. The solid phase begins to melt as it approaches the bottom of the vessel due to the downwardly increasing temperature gradient resulting from condensing of the vapor introduced into the bottom of the crystal melting zone 208d via line 220.

The pressure within the crystal melting zone 208d is greater than the prevailing triple point pressure in the zone due to the pressure head of the liquid above it. Within the zone 208d, the slurry is contacted by the vapor introduced via line 220 from the next lower CWM 210. The condensing vapor is introduced at substantially the pressure prevailing at the bottom of the crystal melting zone 208d, which pressure is maintained at a value slightly above the prevailing triple point pressure in order to minimize the compression work by the compressor 220a, while assuring an adequate driving force for melting crystals at the desired rate.

The condensing vapor is introduced into the zone 208d in an amount sufficient to melt substantially all of the solid phase formed within the crystal forming zone 208b, although a layer of the solid phase may be maintained in the crystal melting zone 208d during continuous steady state operation. In the separation of the carbon dioxide herein, the solid phase and the condensing vapor are both substantially carbon dioxide and the mass flow ratio of condensing vapor melting solid is about 1:1.7 since the heat of vaporization of carbon dioxide is about 6600 B.T.U./lb. mole and the heat of fusion is about 3800 B.T.U./lb. mole. Accordingly, the carbon dioxide-enriched liquid phase within the crystal melting zone 208d comprises about one-third condensed vapor and two-thirds melted solid phase.

A portion of the carbon dioxide-enriched liquid phase produced in the zone 208d is passed to the CWM 210 through line 218 for further crystallization and melting. The remaining portion of the carbon dioxide-enriched liquid phase produced in the zone 208d flows upwardly through the washing zone 208c to wash the downwardly falling solid phase and further concentrate the excluded material in the upper regions of the CWM 208.

In the illustrated embodiment, the depth of the liquid phase in the CWM 208 is about 10 to 15 feet, so that the pressure difference between the top and the bottom of the unit is about 5 to 10 psia. In the purification of the liquid carbon dioxide absorbent, this pressure difference is sufficient for the concentrations of excluded material encountered in the stripping section of the separation, as more fully discussed below.

The WM 200 is substantially filled with solid and liquid phases of the materials to be separated. Accordingly, the WM 200 provides a crystal washing zone 200c extending from the top of the vessel to a lower region therein, where a crystal melting zone 200d is formed. The solid phase is melted in the zone 200d by a condensing vapor introduced through line 224, and a carbon dioxide-enriched liquid phase is produced in this zone in the same manner as described above with respect to the CWM 208. In this instance, a portion of the carbon dioxide-enriched liquid is passed through line 214 to the CWM 206 and the remaining portion of the enriched liquid carbon dioxide is backwashed upwardly through the WM 200 to concentrate the excluded material adjacent the upper regions thereof.

In view of the relatively high concentrations of excluded materials in the WM 200, solid phase is formed in separate flashers 202 and 204. A slurry containing the solid phase is delivered from each of the flashers to the WM 200 at pressures above the highest prevailing triple point pressure in the WM to assure that no vapor phase exists in the upper regions of the WM.

The pressure in the crystal melting zone 200d is maintained at a value just higher than the triple point pressure prevailing in the zone. The pressure decreases in an upward direction as the distance to the top of WM 200 decreases because the pressure head decreases. However, the prevailing triple point pressure decreases even more rapidly in the upward direction because of the rapidly increasing concentration of excluded material, or hydrogen sulfide and other sulfur-containing molecules. Thus, at every position in WM 200 the pressure exceeds the prevailing triple point pressure, and vapor cannot persist in the presence of a mixture of solid and liquid phases.

As the solid phase passes downwardly through the crystal washing zone 200c due to the force of gravity, the pressure increases due to the pressure head of the zone and the temperature is increased due to the latent heat of condensation of the condensing vapor at the bottom of the WM 200. Accordingly, the height of the WM 200 and the pressure head developed by the liquid phase therein are determined by the amount of washing required for the solid phase and the desirability of using one or more intermediate flashers, such as the flasher 204, while assuring that the pressure in the zone 200d is above the prevailing triple point pressure therein. As indicated above, the pressure in the crystal melting zone is preferably just above the prevailing triple point pressure in order to minimize the compression work in providing a condensing vapor from the next lower unit.

The desired overhead product and bottom product flows in view of the feed stream flow will require process designed internal solid, liquid and vapor flows in accordance with the heat of fusion of the solid phase and the heat of condensation of the condensing vapor phase. In order to relieve the burden of the flasher 202 in providing the required flows, it is convenient to use one or more intermediate flashers, such as the flasher 204, in connection with the WM 200. The entire output of such flashers may be returned to the WM at points of matched composition and the use of several flashers at intermediate points along the height of the WM to process liquid streams of different concentrations minimizes the work required to compress and condense the required vapor flow.

As shown in FIG. 4, an intermediate liquid stream is withdrawn from the WM 200 and passed to the flasher 204 through line 240. The flashing of the liquid stream in the flasher 204 provides a solid phase which is returned with a liquid phase of increased concentration of excluded material as a slurry to the WM 200 through line 242, with the aid of a pump. The slurry in line 242 is returned to the WM 200 at a point of matched concentration of the excluded material in the liquid phase of the slurry and that in the liquid phase within the WM 200. The evaporation vapor from the flasher 204 is discharged through line 244, compressed by in-line compressor 244a, condensed by indirect heat exchange in the heat exchanger 212 (shown here in phantom outline for convenience) and returned to the WM 200 through line 246. As shown in FIG. 4, the liquid in line 246 is enriched in carbon dioxide and therefore returned at a relatively lower intermediate point to the WM 200.

The heat exchanger 212 is used in connection with both the flasher 204 and the CWM 210. More particularly, the compressed evaporation vapor from the flasher 204 is cooled in the heat exchanger 212 to use efficiently the refrigeration provided in the exchanger 212 upon evaporation of the liquid phase withdrawn from CWM 210 through line 226 for use as a condensing vapor in the CWM 210. Substantially pure carbon dioxide liquid is also withdrawn from the CWM 210 through line 54; its refrigeration potential is recovered in heat exchanger system 60, and it is recycled via line 51' as condensing vapor for use in the CWM 210. In this manner, the primary refrigeration potential of the liquid removed from CWM 210 in streams 226 and 54 is recovered and the liquid is converted into condensing vapor supplied to CWM 210 via line 228.

In the crystallizer 40', the pumping of reflux and other liquid streams is required. In pumping a liquid stream which is at its triple point temperature, the generation of heat by pump slippage must be minimized and any heat generated must otherwise be dissipated in order to prevent vaporization of the liquid and cavitation in the pump. For these purposes, it has been found practical to submerge the pump in a refrigerated liquid bath maintained at (or close to as possible) the triple point temperature of the liquid being pumped without forming solids in the pumped liquid. Within the bath, a recycle line is connected between the discharge and intake lines to the pump. In a known manner, a back pressure regulator and heat exchanger are placed in the recycle line to condense any vapor which may be present in the liquid being pumped and to remove the heat added by the pump. Further, a somewhat larger than normal net positive suction head is also helpful to minimize cavitation.

Figure 5:
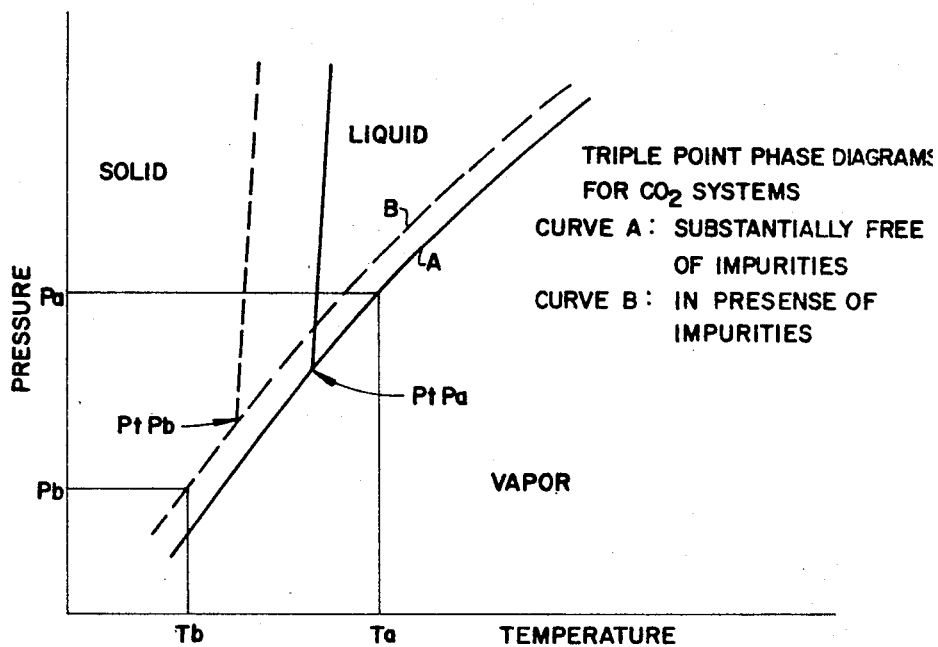
FIG. 5 is a diagrammatic illustration of triple point phase diagrams for carbon dioxide systems as they may exist in the crystallizer of FIG. 4.

Referring to FIG. 5, the variation of the triple point locus conditions in accordance with the composition of the system is diagrammatically illustrated. In FIG. 5, curve A qualitatively illustrates the triple point phase diagram for a carbon dioxide system substantially free of impurities as occurs in the crystal melting zones and curve B illustrates the triple point phase diagram for the system when the concentration of impurities or excluded material is increased as occurs in the crystal forming zones or the upper regions of the CWM's and WM's. The presence of impurities or the excluded material herein depresses or lowers the triple point pressure and temperature in accordance with the relative amount of the impurities or excluded material present in the system. It should be appreciated that small concentration gradients of the excluded material exist in both the crystal forming and melting zones. These concentration gradients are very small as compared with overall concentration gradients established in each of the stages of the cascade and, therefore, it is reasonable to consider the compositions of the materials in the crystal forming and melting zones to be of fixed values despite the small concentration gradients in the zones. Accordingly, the crystal forming and melting zones may each be considered to have a unique triple point pressure and temperature in accordance with the compositions of materials effectively prevailing therein.

The term "triple point" used throughout this application has the conventional meaning of a unique pressure and temperature at which solid, liquid, and gas phases coexist in equilibrium with each other. Normally, the term "triple point" is associated with a single component system, and the fact that there is a unique triple point pressure and temperature is confirmed by the phase rule $$F = C - P + 2$$

where
  $F$ = degrees of freedom (pressure, temperature, compositions)
  $C$ = number of components in the system
  $P$ = number of phases present.

As an example, consider a single component system with solid, liquid, and gas phases present ($C = 1$, $P = 3$). Then by the phase rule $$F = 1 - 3 + 2 = 0$$

there are zero degrees of freedom and there is a unique pressure and temperature at which all three phases coexist.

Now consider a multicomponent system with three phases present. Let n = the number of components in the system, where $n > 1$. The phase rule applied to this system $$F = n - 3 + 2 = n - 1$$

indicates $n - 1$ degrees of freedom. The composition of the system can be fixed by specifying $n - 1$ mole or mass fractions. So, for a fixed composition three-phase system, there will again be zero degrees of freedom, and there is a unique pressure and temperature at which three phases coexist. Consider next the coexistence of only solid and liquid phases. Since $P = 2$, the phase rule applied to this system $$F = n - 2 + 2 = n$$

indicates n degrees of freedom. Specifying the composition fixes $n - 1$ of these n degrees of freedom. Hence, there is one degree of freedom in a system of fixed composition with solid and liquid phases present, corresponding to the nearly vertical line emanating from the triple point. Along this line, solid and liquid can coexist over a range of pressures and corresponding temperatures in equilibrium in a system of fixed composition. Similarly, the solid-vapor line and the liquid-vapor line can be rationalized. Thus, the concepts of (1) a triple point for a multicomponent system of fixed composition, and of (2) triple point pressures and temperatures which vary with the composition of the system are valid and quite useful in characterizing the crystallization process In the CWM's of the illustrated embodiment, economically desirable rates of vaporization and condensation of the in situ heat transfer component require about a 5 to 10 psia pressure differential between the top and bottom of a CWM. Accordingly, each of the CWM's is provided with a height such that the pressure head developed by the slurry in the washing zone between the crystal forming and melting zones is about 5 to 10 psia. In the illustrated embodiment, there is no substantial variation in the triple point pressure in each of the CWM's in the stripping section of the cascade, since the first crystallization separation in the WM reduces the 4 mol percent of hydrogen sulfide and other sulfur-containing gases in the feed stream delivered to WM 200 to about one mol percent as reflected in the liquid flowing in line 214 to CWM 206.

In contrast with the CWM's, it is not convenient to provide the WM 200 with a height sufficient to develop a pressure head required to overcome the difference in triple point pressures between the 25 mol percent overhead vapor product and the enriched carbon dioxide liquid phase in the melting zone 200d, which contains about one mol percent of hydrogen sulfide and other sulfurcontaining molecules. In the illustrated embodiment, the crystal melting zone 200d is maintained at about 75 to 80 psia, which is slightly above the triple point pressure of the enriched carbon dioxide therein and it is provided with a height of about 10 feet for purposes of assuring adequate washing of the crystals and allowing for the use of an intermediate flasher as shown.

With further reference to FIG. 5, it is convenient to illustrate the preferred operating pressure ranges in accordance with the present invention. Assuming curve A is the phase diagram for the crystallizable material at the maximum purity desired in a particular separation, the preferred operating pressure range in the final crystal melting zone of the separation is between the triple point pressure, $Ptp_a$ and $Ptp_a$ plus 30 psia, the latter being qualitatively illustrated in FIG. 5 by the pressure $P_a$. Similarly, assuming curve B is the phase diagram for the maximum concentration of excluded material which will have to be evaporated in order to obtain a desired excluded material product which may comprise the mother liquor or be contained in the evaporated vapor phase, the preferred operating pressure range in the crystal forming zone is between the prevailing triple point pressure, $Ptp_b$ and the higher of 0 psia or $Ptp_b$ minus 30 psia. In FIG. 5, this minimum preferred operating pressure is indicated by the pressure $P_b$. Accordingly, in the assumed separation, the operating pressure range is between $P_b$ and $P_a$, and the operating temperature range is between $T_b$ and $T_a$, which are the corresponding temperatures at equilibrium conditions for the respective pressures.

As the crystallizable material or carbon dioxide moves downwardly through lines 214, 216, and 218 in the stripping section, it is being passed from a region of higher pressure to one of lower pressure. Accordingly, it is convenient to directly flash the liquid into the crystal forming zone of the CWM to which it is being passed. The solid phase obtained from flashing the liquid streams contributes to the provision of the solid phase in the crystal forming zone. It is not necessary that these liquid streams be flashed as they are introduced into their respective CWM's, since the removal of evaporation vapor from the vapor space in each of the CWM's will assure the provision of the required solid phase.

Referring to FIG. 6, a single-stage crystallizer 250 comprising a CWM 252 and a heat exchanger 254 is shown. In some applications, as for example in the case of a liquid carbon dioxide feed containing about 1% by weight hydrogen sulfide, and where a purity of only 0.01% to 0.1% hydrogen sulfide is needed, a single-stage will be sufficient to produce this purity. The overhead product obtained in this case will contain about 2% or 3% hydrogen sulfide.

The operation of the CWM 252 is similar to the CWM's discussed above. Accordingly, a vapor space 252a is located above a free surface 253 of the liquid phase of the materials within the vessel. Further, a crystal forming zone 252b, a crystal washing zone 252c, and a crystal melting zone 252d are formed within the liquid phase in the CWM 252. In FIG. 6, only the solid phase is shown within the liquid phase, the vapor phase being omitted for purposes of clarity.

In the crystallizer 250, the liquid carbon dioxide feed is introduced into the CWM 252 through the line 256 at an intermediate location of matched liquid composition. The solid phase is formed by evaporative cooling and the evaporation vapor is removed through overhead line 258. The purified carbon dioxide is withdrawn from the bottom of CWM 252 through line 260 with the aid of a pump (not shown). The carbon dioxide flowing in line 260 is divided to provide a bottom product which is withdrawn through line 260a, and the remaining portion of the withdrawn carbon dioxide is passed via line 260b to heat exchanger 254, wherein it is vaporized by means of indirect heat exchange. The vapor is returned through line 262 to the crystal melting zone 252d for melting the solid phase. Accordingly the condensing vapor in a single stage system is derived from the evaporation of a crystallizable material-enriched liquid, as is the case in multiple stage, series connected systems.

The CWM 252 includes a number of structural features which are particularly useful in larger diameter vessels. Accordingly, the structural features of the CWM 252 described below are useful in the CWM's of the crystallizer 40'.

In the CWM 252, an upper stirrer assembly 264, including a plurality of axially spaced impellers 265, is disposed in the crystal forming zone 252b and driven by an external motor (not shown) to aid the production of the solid phase. Proper agitation can aid in increasing the rate of production of solid phase, controlling the size of the solids, transporting solids from the space 252b to zone 252c, and achieving uniform dispersion over the cross-sectional area of the CWM. Standard wall baffles 266 adjacent the stirrer assembly 264 may be a desirable aid to the agitation.

A plurality of axially extending baffle tubes 268 are disposed in the crystal washing zone 252c in order to minimize axial dispersion of the slurry within the crystal washing zone 252c and provide a relatively quiescent washing condition. The baffle tubes 268 are arranged in an axially extending array and may, for example, comprise 2-inch diameter tubes spaced on 4-inch centers. The diameters of the baffle tubes 268 are exaggerated in FIG. 6 for clarity of illustration. In commercial applications, the CWM 252 may be 10 to 15 feet tall and have a 10-foot diameter so as to have a length-to-diameter ratio (L/D) of 1 to 1.5 in the crystal washing zone 252c in the absence of a baffle arrangement. In contrast, the baffle tubes 268 provide an L/D ratio much greater than 10 in the crystal washing zone 252c in order to minimize axial dispersion.

A lower stirrer assembly 270, including axially spaced impellers 271, is located in the crystal melting zone 252d. The stirrer assembly 270 is driven by an external motor (not shown), and it serves to promote the melting of the solid phase and the condensation of the condensing vapor within the zone. The stirrer also helps to provide a uniform backwash flow of liquid from the zone 252d throughout the cross sectional area of the CWM. In order to minimize the swirling of the liquid phase due to the rotation of the stirrer assembly 270, four wall baffles 272 (only two being shown) are fixed at equal angular positions about the inside periphery of the CWM 252 adjacent the crystal melting zone 252d.

As shown in FIG. 6, it is convenient to dispose a perforated member 274 adjacent the bottom of the crystal melting zone 252d for purposes of limiting the further downward movement of the solid phase and minimizing the possibility of withdrawing solid through the line 260. The use of perforated member 274 to possibly avoid direct contact between the solid phase and the condensing vapor is within the scope of the invention and contemplated as a means of melting solid phase by direct heat transfer with a condensing vapor. It should also be appreciated that the crystal melting zone in the CWM or in a WM can be provided in a separate vessel by withdrawing a slurry from the bottom of the CWM or WM and introducing the condensing vapor into such separate vessel to melt the solid phase of the slurry. The liquid phase obtained upon melting the solid phase in the separate vessel is divided between a backwash flow and a liquid stream which is vaporized to provide a condensing vapor in a single stage application, as in FIG. 6, or a liquid stream which is passed to another crystallizing stage, as in FIG. 4.

The novel crystallization process may also be used in a single-stage application to concentrate an excluded material, such as hydrogen sulfide, to provide a feed for a Claus plant as described above, and to provide only a relatively pure crystallizable material output which is satisfactory for use as a refrigerant in indirect heat transfer. For these purposes, a single-stage crystallizer 276 as shown in FIG. 7 may be used. The crystallizer 276 comprises a WM 278, a heat exchanger 280, and optionally a flasher 282 and/or one or more additional flashers or sources of liquid or slurry 284 and 286. In FIG. 7, only the solid phase is diagrammatically shown within the liquid phases in the flasher 282 and WM 278.

The operation of the WM 278 is similar to that of the WM 200 described above, and, similarly, includes a crystal washing zone 278c extending from the top of the vessel to a lower region therein where a crystal melting zone 278d is formed. The relatively purified carbon dioxide is withdrawn from the bottom of the WM 278 through line 288 with the aid of a pump (not shown). The withdrawn carbon dioxide is divided to provide a bottom product which is withdrawn through line 288a. The remaining portion of the withdrawn carbon dioxide is passed through line 288b to the heat exchanger 280, wherein it is vaporized. The vapor is passed via line 290 to the crystal melting zone 278d.

A liquid stream is withdrawn from the upper regions of the WM 278 and passed via line 292 to the flasher 282. In the flasher 282, a vapor space 282a is maintained above the liquid phase of the materials therein and evaporation vapor is withdrawn through line 294. The removal of evaporation vapor causes evaporative cooling of the liquid phase in the flasher and the formation of a crystal forming zone 282b. The solid phase formed in the zone 282b passes downwardly and is withdrawn as a slurry through line 296 with in-line pump 298 and returned to the top of the WM 278.

In the crystallizer 276, the excluded material-enriched product may be withdrawn as a component of the evaporation vapor removed through line 294. If the excluded material is not a component of the evaporation vapor, the excluded material-enriched product may be withdrawn as a liquid stream from the liquid phase in the flasher 282 through line 300. If no flashers are used in the crystallizer 276, the excluded material-enriched product may be withdrawn as a liquid stream through line 292.

As shown in FIG. 7, the WM 278 is provided with stirrer and baffle arrangements functionally similar to those used in the CWM 252, but with some structural modifications to accommodate the possible use of a number of flashers or sources of liquid or slurry 284, 286, which may be introduced at intermediate locations spaced from the top of the WM. However, identical reference numerals are used for the stirrer and baffle arrangements with the addition of a prime designation and the particular modifications are described below.

The stirrer assembly 264' includes two upper impellers 265' located adjacent wall baffles 266' for purposes of distributing the solid phase introduced into the WM 278 adjacent the upper regions thereof. Accordingly, the slurry from the flasher 282 and the input from source 284 are accommodated in this manner. For purposes of illustration, the flasher or source of liquid or slurry 286 is located at an intermediate point along the axial length of the WM 278. To distribute the input from the flasher or source 286, the axial extent of the baffle tubes is interrupted and an upper set of baffle tubes 268'a and a lower set of baffle tubes 268'b are provided. Further, the shaft of the stirrer assembly 264' is extended to a point between the upper and lower baffle tube assemblies and a further, intermediate impeller 265' is provided together with associated wall baffles 266'. The intermediate impeller 265' effectively distributes the material introduced from the flasher or source 286 with only a minimum disturbance of the quiescent axial flow desired in the crystal washing zone 278c. Consequently, effective washing of the solid phase is maintained in both the upper baffle tubes 268'a and lower baffle tubes 268'b. It should be appreciated that a similar interruption of the baffle tubes 268 in the CWM 252 of FIG. 6 may be employed when an intermediate reflux stream is to be introduced into the CWM. As an alternative to the axially extending baffle tube 268, 268'a and 268'b, it is also presently contemplated that a plurality of spaced, generally horizontally extending, perforated baffles may be used. In this instance, one or more impellers may be located between adjacent baffles at points where streams are introduced into the vessel.

In the illustrated purification of carbon dioxide, there is a tendency for solid deposits to adhere to the interior surfaces of the vessels adjacent the crystal forming zones and the free surfaces of the liquid phases. These deposits especially tend to develop at relatively high purities of carbon dioxide in the CWM's adjacent the lower portion of the cascade, and the deposits can cause blockage if allowed to grow unchecked. Mechanical scraping and/or agitation as illustrated in the embodiments of FIGS. 6 and 7 for somewhat different purposes can be used to ameliorate this problem. In order to resolve this problem more conveniently, small amounts of additives can be directly added to the system. Such additives should be liquids miscible with liquid carbon dioxide The additives should also have low viscosity, low vapor pressure, good stability, and in mixtures with carbon dioxide a range of freezing points below $-56.6°$ C. All of the liquids listed earlier in the main gas separation process as examples of liquids useful in forming refrigerant absorbents comprising a liquid vehicle and solid carbon dioxide are examples of liquids useful as additives to ameliorate solid carbon dioxide deposits in the crystal forming zones. The additives act as impurities and aid the melting of any crystals forming on the walls adjacent crystal forming zones in the CWM's or flashers. In the illustrated embodiment, the additives are carried upwardly in the liquid phase as an impurity and concentrated in each of the crystal forming zones. The additives do not evaporate since their vapor pressures are much lower than that of carbon dioxide, and they remain liquid, concentrated in the crystal forming zones or at the tops thereof, in a most effective manner to prevent the formation of solid carbon deposits on the walls of the CWM's or flashers.

As indicated above, the additives move upwardly through the crystallization process and are concentrated with the primary impurities. Thus, a region of concentrated additive, which may be about one foot in depth, is formed above the crystal forming zone in the liquid phase. Thus, the crystal forming zone may be spaced from the free surface of the liquid phase by a distance equal to the depth of the region. A region of concentrated additive 302 is shown in FIG. 6 above the crystal forming zone 252b in the CWM 252 and, in FIG. 7, a similar region of concentrated additive 304 is shown in the flasher 282 above the crystal forming zone 282b. When an additive is used in the separation process in the crystallizer 40', there are similar regions of concentrated additive formed above each of the crystal forming zones in the CWM's 206, 208, and 210 as well as above crystal forming zones in the flashers 202 and 204.

A region of concentrated additive 203 in flasher 202 is diagramatically shown in FIG. 4.

The exact mechanism by which the additives work is not presently known, but it has been observed that their presence leads to a relative increase in temperature in the regions of concentrated additive. For example, the upwardly decreasing temperature gradient in the zones of the CWM 208 of FIG. 4 may be as follows:

Additive Region—56° C.
Zone 208b—58° C.
Zone 208c—57° C.
Zone 208d—56° C.

Accordingly, the sufficiency of the amount of additive in each stage may be determined by monitoring the temperature gradient as well as by visual sight glass inspection.

Referring to FIG. 4, the additive collects in the region 203 in the flasher 202 as it moves upwardly through the cascade and it is necessary to recycle the additive to the lower units of the cascade. The additive is recycled by withdrawing a liquid stream through line 306 from the region 203. The withdrawn stream comprising additive, hydrogen sulfide, and carbon dioxide may be separated by distillation, flashing, or other means. In the embodiment of FIG. 4, a distillation system 308 is used. The hydrogen sulfide and carbon dioxide components are separated as a top product and withdrawn through line 310 and added to the overhead product being withdrawn from the crystallizer 40' through line 50. The additive is withdrawn as a bottom product from the distillation system 308 through the line 312 and returned to the lowermost CWM 210 through line 312a.

The additive may be derived in whole or in part as a component in the feed to the crystallizer. For example, the precooling and dehydration system 20 of the main gas separation process may include as a conventional water scavenging step the use of a slightly volatile solvent, such as methanol, to absorb water. Added or residual methanol in the main gas stream passes through the sulfur absorber 30 and the stripper absorber 35 with the carbon dioxide, and it is delivered to the crystallizer 40' as a component in the feed line 39a.

In the crystallizer 40', the methanol will serve as an additive, and it will be passed upwardly through the cascade. In view of the continuous introduction of the methanol additive in this instance, the additive flowing through line 312 is divided, a portion of the additive being delivered to the CWM 210 via line 312a, and the remaining portion of the additive being returned to the precooling and dehydration system 20 via line 312b.

In some applications of the crystallizer 40' or similar cascaded arrangements, the excluded material may be moved upwardly by the vapor flows between units in sufficient amounts to permit the elimination of reflux streams, such as those in lines 230, 232, and 234. In such applications, an appropriate amount of additive is added to each of the CWM's and WM's (or directly to flashers associated with the WM's), and the additive will be retained in each of the units since it will not pass upwardly with the vapor. If the additive is derived in whole or in part as a component in the feed to the crystallizer in such applications, the line 306 may be relocated to remove the concentrated additive from the stage to which the crystallizer feed is added and the line 312a may be branched to periodically deliver additive to those stages requiring additional additive as may be determined by monitoring the temperature above the crystal forming zones.

In addition to separating carbon dioxide and concentrating hydrogen sulfide in the acid gas separation process, as illustrated above, the novel crystallization process is also applicable to other systems. Initially, pertinent separation systems may be generally characterized by consideration of the relative volatility ratio, "$\alpha$", of the system. The relative volatility $\alpha$ is the ratio of the gas-liquid solubilities or vapor liquid equilibria constants, K, of the materials (for example, materials 1 and 2) to be separated as represented by the formula:

$$\alpha = \frac{K_1}{K_2} \qquad (6)$$

where, $K = y/x$ for each of the materials, y is the mole fraction of the material in the vapor phase and x is the mole fraction of the material in the liquid phase, with equilibrium between the vapor and liquid phases. The K constants are functions of the overall composition of the system and either the pressure or temperature and, therefore, the relative volatility ratio of the system will differ at various locations throughout the crystallization separation process in accordance with the prevailing overall composition of the system, pressure and temperature at a particular location in the process. In the following discussion of crystallization systems and illustrative examples thereof, the relative volatility is considered in terms of the ratio of the K value of the excluded material divided by the K value of the crystallizable material.

The relative volatility ratios for a number of crystallization systems are reported in the table immediately below. In those cases where a single ratio is reported, the reported ratio is the relative volatility of the system at the crystallizable material output end of the process. In those cases where the relative volatility is expressed as a range, the first reported value is the ratio at the crystallizable material output end of the process and the second value is the ratio at the excluded material output end of the process. The ratio, as reported at either end of the process, is based upon a concentrated system wherein either the crystallizable material or the excluded material is present at a concentration in the range of 80% to 90%. In all cases, the ratios are reported at a pressure of about 6.7 atmospheres and a temperature of about $-50°$ C. unless otherwise indicated.

| System | Relative Volatility Ratio ($\alpha$) |
|---|---|
| $H_2S/CO_2$ | 0.72 |
| $C_2H_6/CO_2$ | $2.78 > \alpha > 0.27$ |
| $C_2H_4/CO_2$* | $1.63 > \alpha > 0.83$ |
| $C_3H_8/CO_2$** | ~0.1 |
| $COS/CO_2$ | 0.34 |
| $O_2/CO_2$ | >50 |
| $H_2/CO_2$ | >500 |
| $NaCl/CO_2$ | 0 |

*Determined at about 0° C.
**Determined at about $-40°$ C.

The data in the foregoing table illustrates the broad applicability of the crystallization process for effecting the separation of the components of various systems. The relative volatility ratio is conveniently used to identify those systems wherein distallation is not practical or possible.

As noted above in connected with prior art desalination, the novel process herein may be used to separate an excluded material having an appreciable vapor pressure which results in the excluded material being present in the evaporation vapor. Thus, the novel process is distinguished over prior art desalination by applicability to systems having a relative volatility $\alpha \geq 0.1$, as contrasted with prior art desalination wherein $\alpha = 0$.

The subject process is also applicable to systems which are not readily separated by distillation techniques in an economically practical manner. Thus, the crystallization process is useful in systems which during the course of the separation have a relative volatility ratio in the range of $0.3 \leq \alpha \leq 3.0$, the usefulness of distillation in such systems being highly questionable, and the subject process is especially advantageous in systems wherein $0.5 \leq \alpha \leq 2.0$, distillation generally being deemed unsuitable to effect separation of such systems. Within the indicated ranges of relative volatilities, the capital costs of distillation are significantly increased by the relatively large number of stages required to effect the separation. Of course, separation by distillation is not possible at a relative volatility ratio of 1.0 which characterizes the formation of an azeotrope by the materials being separated. Regardless of the relative volatility of a particular system, crystallization is a preferred separation technique over distillation whenever it is desirable not to heat the system materials. Energy fluxes are usually smaller for crystallization than for distillation, since the heat of fusion is less than the heat of vaporization.

In illustration of particular systems, the crystallization process may also be used to separate a liquid carbon dioxide absorbent from one or more absorbed noble gases such as xenon and krypton following the absorption of such noble gases by the liquid carbon dioxide absorbent. The absorption of noble gases by carbon dioxide is disclosed in U.S. Pat. Nos. 3,850,593, dated Nov. 26, 1974, and 3,742,720, dated July 3, 1973. Thus, a gas mixture contaminated with noble gases may be passed through the absorption system 30 for contact with the liquid carbon dioxide absorbent to provide a purified overhead product. The carbon dioxide absorbent and absorbed noble gases may then be passed to the crystallizer 40' for separation of the cabon dioxide and concentration of the noble gases.

The crystallization process is readily applied to an ethane and carbon dioxide system. In this system, ethane is the impurity or excluded material in the crystallization process and carbon dioxide is again separated as the crystallizable material and functions as the in situ heat transfer component. Ethane is slightly more volatile than hydrogen sulfide and, accordingly, the upward flowing vapor streams contain more ethane. Thus, the flow of liquid reflux within lines 230, 232, and 234 can be reduced or eliminated. Essentially, pure carbon dioxide is produced as a bottom product and a stream of ethane-carbon dioxide is produced as a top product. The concentration of the ethane in the top product may readily be as high as 75 mol percent.

In contrast, distillation has limited utility for separating mixtures of ethane and carbon dioxide, since a low boiling azeotrope is encountered. The composition of this azeotrope ranges from about 30% to about 40% ethane on a molar basis, depending on the pressure, 30% at 50 atmospheres and 40% at 10 atmospheres. Thus, a feed containing about 10% ethane can be distilled into about a 35% ethane top product and a 100% carbon dioxide bottom product, but pure ethane cannot be produced.

In order to obtain substantially pure ethane and pure carbon dioxide, the subject crystallization process can be combined with distillation. For example, the 10% ethane feed can be introduced into the crystallization cascade to provide a substantially pure carbon dioxide bottom product and a 75% ethane top product. The top product is then distilled to provide a substantially pure ethane bottom product. The azeotrope, about 35% ethane, is removed from the top of the distillation column and recycled back to the crystallization cascade. Accordingly, the combination of crystallization and distillation allows the production of both pure carbon dioxide and pure ethane products.

The crystallization process may be applied to systems other than those using carbon dioxide as the in situ heat transfer component. For example, the process may be used to purify sulfur hexafluoride in a system contaminated with hydrogen sulfide or hydrocarbons which depress the freezing point of sulfur hexafluoride. Sulfur hexafluoride is commercially used as a gaseous dielectric for high voltage power applications. In this instance, the sulfur hexafluoride is analogous to the carbon dioxide in the crystallization process, since it is simultaneously separated as the crystallizable material and serves as an in situ heat transfer component. The physical and thermodynamic properties of sulfur hexafluoride are similar to those of carbon dioxide. The triple point of pure sulfur hexafluoride occurs at a pressure of 32.5 psia and at a temperature of $-50.8°$ C. At triple point conditions, the heat of fusion of sulfur hexafluoride is 2600 BTU/lb. mole (carbon dioxide, 3800 BTU/lb. mole) and the heat of vaporization is 6600 BTU/lb. mole (carbon dioxide, 6600 BTU/lb. mole). The surface tension and viscosity of liquid sulfur hexafluoride, like those of liquid carbon dioxide, are quite low.

The crystallization process is also well suited to the separation of para xylene from meta xylene and ortho xylene. Para xylene has a freezing point of 13.3° C., meta xylene is $-47.9°$ C., and ortho xylene is $-25.2°$ C. The crystallizable material in this separation is para xylene, and the impurities or excluded materials are meta xylene and ortho xylene, which are substantially rejected from the crystal phase. Thus, conventional crystallization using heat exchange surfaces is feasible and is practiced. However, the mixed xylene isomers by themselves cannot be conveniently separated in the subject crystallization process, since the vapor pressure of the mixture is too low to provide a reasonably dense vapor phase. Accordingly, it is necessary to include in the system an in situ heat transfer component such as carbon dioxide, sulfur hexafluoride, or a low molecular weight hydrocarbon for purposes of increasing the vapor presssure and the vapor phase density.

In a resulting carbon dioxide system, the carbon dioxide as the in situ heat transfer component will be the major component of the vapor streams flowing upward from vessel to vessel in the cascade. The excluded materials, ortho and meta xylene, will be carried upward from vessel to vessel primarily by liquid reflux streams. The para xylene crystals melted with the condensing carbon dioxide vapor provide a downward flowing liquid mixture of para xylene and carbon dioxide. The final liquid product consisting of para xylene and carbon dioxide is separated in a final flashing step in this instance. The liquid resulting from the flashing is pure para xylene product, and the carbon dioxide in situ heat transfer component is removed as a vapor from the flasher and it contains a small amount of para xylene. This is recycled back into the crystallization process; a convenient point of recycle is into the mixed xylene isomer feed.

Alternative Crystallization Process Summary

The foregoing separation systems illustrate the broad applications of the improved crystallization process herein. As particularly illustrated by the xylene isomer separation, the separation system itself may be initially designed to include an in situ heat transfer component. In many instances, it is practical or desirable to add a material to the system to specifically serve as an in situ heat transfer component. To a large degree, the addition of a specifically added material is dependent upon the triple point vapor pressures of the mixtures of materials to be separated over the range of compositions to be encountered. If the triple point vapor pressures of the mixtures of materials to be separated are sufficiently high to enable a reasonably dense gas phase and reasonable levels of heat transfer, an added in situ heat transfer component may not be needed and the vapor phase of the mixture of the crystallizable material and the excluded material may directly serve as the heat transfer component of the system. In this instance, the crystallizable material is the primary component of the vapor phase and it is condensed during the crystal melting step to release its latent heat of condensation. If the triple point vapor pressure of the mixtures of crystallizable material and excluded material is not sufficiently high, a material to serve as an in situ heat transfer component is added to the system. The in situ heat transfer component selected will be relatively more volatile than the other materials in the mixture or system, and it may comprise substantially the sole component, a primary component, or a lesser but significant component of the vapor phase of the system. Thus, the in situ heat transfer component may be the crystallizable material or a material specifically included in the system for purposes of in situ heat transfer, or a combination of the foregoing and, in each case, the in situ heat transfer component may include a lesser amount of the excluded material or materials.

As indicated, the main criteria for selecting suitable in situ heat transfer components include that the mixture or system resulting from adding the heat transfer component should have convenient triple point locus conditions, particularly with respect to pressures, which must be high enough to ensure reasonably dense triple point locus vapor. Further, the added component is preferably excluded from the solid phase, although this criterion is not essential. The in situ heat transfer component should be separable from the crystallizable material by some subsequent separation such as flashing, distillation, liquid-liquid extraction, or other means. Preferably, the added component should be miscible with the mixture, or, if not miscible, its liquid phase should be less dense than the liquid phase of the crystallizable material plus the excluded material. Lastly, the enthalpy difference between the heat transfer component in solution or liquid phase and its vapor phase should be large.

As indicated, it is not necessary that the excluded material be contained in the vapor phase, since the required mass flows may be provided by liquid reflux streams while continuing to effect substantially all of the required heat transfer between stages through the use of the in situ heat transfer component. If the vapor phase does not include the excluded material, or if it only includes an insufficient amount for purposes of mass flow, the required mass flow of the excluded material from stage to stage in the cascade may be provided in whole or in part by appropriate liquid reflux streams which carry negligible energy for melting and freezing. In all cases, it is not necessary to separate or specifically handle substantial quantities of the crystal phase and, to the extent that the crystal phase is conveyed within the rectifying section of the process, it is conveyed in the form of a slurry so as to facilitate handling.

In generally applying the crystallization process to a given system, the triple point locus conditions of the system over the range of compositions to be encountered should include a reasonably high pressure which avoids rarefaction of the vapor phase and enables acceptable levels of material and/or heat transfer by the vapor phase. Thus, it is generally desirable that the triple point pressure of the system be about 1.0 atmospheres or greater. The following organic materials have triple point pressure values of about 1.0 atmospheres or greater: $C_2Cl_6$, $C_2H_2$, $C_6Cl_4O_2$, $C_6H_{12}O_3$ and CFN. The following inorganic materials have triple point pressure values of about 1.0 atmospheres or greater: $UF_6$, $SF_6$, $AlCl_3$ and $CO_2$.

The viscosity of the liquid mixture should be reasonably low to permit suitable liquid flow rates as required in the process. As a practical matter, the liquid phases of the crystallizable material and excluded material will usually be miscible within the range of concentrations contemplated in the intended application of the crystallization process. However, it should be appreciated that the crystallization process is also effective in immiscible systems.

Final Summary

From the foregoing description of this invention, it will be appreciated that it enables the complete separation of sulfur-containing gases from relatively low boiling point gases, and any desired degree of separation of other relatively high boiling point gases, including carbon dioxide, from lower boiling point gases, while operating over a wide range of main gas stream pressures. As capital equipment and operating cost analyses will further show, these results may be achieved with substantial savings in both categories compared to the capital equipment and operating costs of other processes heretofore available for obtaining the same or comparable results, and these savings may be realized over broad ranges of main gas stream operating pressures and compositions. In addition, the process of the invention has the many other practical and economic advantages set forth in the foregoing Summary of the Invention.

The final purified gas product of the exemplary embodiment of the invention described in detail above is suitable for direct use as a relatively low B.T.U. fuel or for use as a feed to a plant producing relatively high B.T.U. fuel. Depending upon the particular crude gas mixture to be purified by the process of the invention, many other uses for the purified product exist, as will be appreciated by those skilled in the pertinent arts.

The improved crystallization process disclosed herein further enables purification of carbon dioxide for use in the acid gas separation process and concentration of separated sulfur-containing gases to provide a valuable byproduct. Moreover, the crystallization process is broadly useful to effect separation by crystallization in a wide range of systems which, if necessary or desirable, can be initially modified by the addition of an in situ heat transfer agent to utilize or more effectively utilize the novel crystallization techniques.

Although the invention has been described with detailed reference to specific embodiments thereof and to certain optional modifications of the embodiments, it will also be appreciated that the invention is susceptible to many other modifications while utilizing the principles thereof and operating within the scope of the appended claims.

What is claimed is:

1. A process for the removal of contaminant gas molecules from a gas stream, comprising the steps of:
   (1) contacting the gas stream in countercurrent flow with a liquid carbon dioxide absorbent to absorb and entrain the contaminant molecules;
   (2) separating a substantially decontaminated residual gas stream from a mixture of the carbon dioxide absorbent and absorbed contaminant molecules;
   (3) separating the carbon dioxide absorbent and concentrating the contaminant molecules of said mixture by crystallization; and
   (4) reusing at least part of the separated carbon dioxide absorbent as absorbent in step (1).

2. A process as set forth in claim 1, wherein said crystallization of step (3) comprises performing in each of one or more separation stages, comprising the steps of:
   (a) forming a liquid mixture of said carbon dioxide absorbent and absorbed contaminant molecules;
   (b) forming a solid phase containing said carbon dioxide absorbent and at least partially excluding said absorbed contaminant molecules by evaporating said liquid mixture;
   (c) melting said solid phase by direct heat transfer with a condensing vapor; and
   (d) moving said separated carbon dioxide absorbent in a first flow direction to provide a carbon dioxide absorbent-enriched output and moving said contaminant molecules in a second flow direction to provide a contaminant molecule-enriched output.

3. A process as set forth in claim 2, wherein said contaminant gas molecules comprise molecules of at least one or more noble gases.

4. A process as set forth in claim 2, wherein said contaminant gas molecules comprise molecules of at least one or more gases selected from the group consisting of krypton and xenon.

5. A process as set forth in claim 2, wherein said condensing vapor is a vapor phase of a carbon dioxide absorbent enriched liquid mixture located in said process remote of the stage wherein said solid phase is being melted.

6. A process for the removal of sulfur-containing gas molecules from a gas stream, comprising the steps of:
   (1) contacting the gas stream in countercurrent flow with a liquid carbon dioxide absorbent to absorb and entrain the sulfur-containing molecules;
   (2) separating a substantially desulfurized residual gas stream from a mixture of the carbon dioxide absorbent and absorbed sulfur-containing molecules;
   (3) separating the carbon dioxide absorbent and concentrating the sulfur-containing molecules of said mixture by crystallization; and
   (4) reusing at least part of the separated carbon dioxide absorbent as absorbent in step (1).

7. A process as set forth in claim 6, wherein said crystallization of step (3) comprises performing in each of one or more separation stages, the steps of:
   (a) forming a liquid mixture of said carbon dioxide absorbent and absorbed sulfur-containing molecules;
   (b) forming a solid phase containing said carbon dioxide absorbent and at least partially excluding said absorbed contaminant molecules by evaporating said liquid mixture;
   (c) melting said solid phase by direct heat transfer with a condensing vapor; and
   (d) moving said separated carbon dioxide absorbent in a first flow direction to provide a carbon dioxide absorbent-enriched output and moving said contaminant molecules in a second flow direction to provide a contaminant molecule-enriched output.

8. A process as set forth in claim 7, wherein substantially all of the heat energy required for melting said solid phase is provided by said condensing vapor.

9. A process as set forth in claim 7, wherein substantially all of the cooling required to form said solid phase is provided by evaporation of said liquid mixture.

10. A process as set forth in claims 7, 8, or 9, wherein said condensing vapor is a vapor phase of said carbon dioxide absorbent and absorbed sulfur-containing molecules.

11. A process as set forth in claim 7, wherein said crystallization step includes a first stage connected in series to a second stage and providing substantially all mass and energy flows between stages as liquid and vapor phases of said carbon dioxide absorbent and absorbed sulfur-containing molecules.

12. A process as set forth in claim 7, wherein substantially all of the cooling required to form said solid phase is provided by evaporation of said liquid mixture, substantially all of the heat energy required for melting said solid phase is provided by said condensing vapor, and said condensing vapor comprises a vapor phase of said carbon dioxide absorbent and absorbed sulfur-containing molecules.

13. A process as set forth in claim 12, including forming in said liquid mixture solid and liquid flows of said carbon dioxide absorbent and sulfur-containing molecules in accordance with their respective flow directions and corresponding increasing concentration gradients thereof, performing step (b) in a crystal forming zone of said liquid mixture having a relatively high concentration of said sulfur-containing molecules and at a first operating pressure below the prevailing triple point pressure, performing step (c) in a crystal melting zone of said liquid mixture having a relatively high concentration of said carbon dioxide absorbent and at a second operating pressure above the prevailing triple point pressure, forming a crystal washing zone in said liquid mixture extending between said crystal forming and melting zones, moving said solid phase from said crystal forming zone through said crystal washing zone to said crystal melting zone, melting substantially all of said solid phase to enrich the liquid mixture in said crystal melting zone with carbon dioxide absorbent, withdrawing a portion of the liquid mixture in said crystal melting zone to provide said carbon dioxide absorbent-enriched output, and passing a further portion of the liquid mixture to said crystal washing zone to countercurrently wash said solid phase, and withdrawing said sulfur-containing molecule-enriched output as a component in said evaporation vapor, or as a liquid stream withdrawn from said crystal washing zone or said crystal forming zone, or as a combination thereof.

14. A process as set forth in claim 13, wherein said crystallization step includes a first stage connected in series to a second stage, passing a carbon dioxide absorbent-enriched output of said first stage as a liquid stream to said second stage to augment a second stage liquid mixture therein, passing a second stage sulfur-containing molecule-enriched output to said first stage to augment a first stage liquid mixture therein and passing a second stage evaporation vapor to said first stage to provide a condensing vapor therein.

15. A process for the removal of sulfur-containing gas molecules from a feed gas stream, comprising precluding the need to distill the feed gas stream by the steps of:
   (1) contacting the gas stream in countercurrent flow with a liquid carbon dioxide absorbent to absorb and entrain the sulfur-containing molecules;
   (2) separating a substantially desulfurized residual gas stream from a mixture of the carbon dioxide absorbent and absorbed sulfur-containing molecules; and
   (3) separating the carbon dioxide absorbent and concentrating the sulfur-containing molecules of said mixture by crystallization.

16. A process for treating a feed gas stream comprising relatively high boiling point gases including hydrogen sulfide, carbonyl sulfide, and carbon dioxide and relatively lower boiling point gas of primary value, comprising precluding the need to distill the feed gas stream by the steps of:
   (a) providing a feed gas stream which is pressurized and cooled to a predetermined pressure and temperature;
   (b) providing an absorption column and a supply of substantially pure liquid carbon dioxide absorbent at substantially said predetermined pressure and temperature;
   (c) introducing absorbent from said supply thereof and said feed gas stream into said absorption column for separation of said hydrogen sulfide and carbonyl sulfide from said lower boiling point gas;
   (d) contacting said feed gas stream in said absorption column with a countercurrent flow of absorbent in an amount sufficient, but not exceeding that required, to absorb and entrain substantially all of said hydrogen sulfide present in the gas stream and thereby also to absorb and entrain substantially all of said carbonyl sulfide in the gas stream while maintaining most of the absorbent in the liquid state at substantially said pressure and temperature, the balance of the absorbent being vaporized by the heat of condensation of the absorbed gas;
   (e) withdrawing from said absorption column a substantially completely desulfurized residual gas stream containing said relatively lower boiling point gas and a mixture of the still liquid absorbent and gases absorbed or entrained therewith; and
   (f) recovering substantially pure carbon dioxide from the separated liquid mixture of said absorbent and gases absorbed or entrained therewith.

17. A process according to claim 16, in which both the feed gas stream and liquid carbon dioxide absorbent are brought into contact in step (d) at substantially the same temperature and pressure and said temperature is substantially the dew point temperature of carbon dioxide in the feed gas stream at that pressure.

18. A process according to claim 16, in which said feed gas stream is provided with a carbon dioxide dew point temperature above the carbon dioxide triple point temperature.

19. A process according to claim 16, including the step of recovering substantially pure carbon dioxide from said substantially completely desulfurized residual gas stream and returning at least a portion of the recovered carbon dioxide to said absorption column for reuse as absorbent in step (d).

20. A process according to claim 16, in which the substantially completely desulfurized residual gas stream withdrawn from said absorption column in step (e) is cooled to condense carbon dioxide therefrom and the so-condenzed carbon dioxide reflux is returned to the process and used as part of the absorbent in step (d).

21. A process according to claim 20, in which step (e) is performed by withdrawing the substantially completely desulfurized residual gas stream from the top of said absorption column and the mixture of still liquid absorbent and the gases absorbed or entrained therewith from the bottom of the column.

22. A process according to claim 16, in which said relatively lower boiling point gas comprises a major portion of said feed gas stream.

23. A process according to claim 16, in which said feed gas stream includes at least one additional gas of relatively lower boiling point selected from the group consisting of hydrogen, carbon monoxide, nitrogen, and methane, and said relatively lower boiling point gases comprise a major portion of said feed gas stream.

24. A process according to claim 16, in which said feed gas stream consists essentially of hydrogen, carbon monoxide, nitrogen, and methane, together with said hydrogen sulfide, carbonyl sulfide, and carbon dioxide.

25. A process according to claim 16, in which step (a) includes cooling said feed gas stream to said predetermined temperature.

26. A process for treating a feed gas stream comprising relatively high boiling point gases including hydrogen sulfide, carbonyl sulfide, and carbon dioxide and relatively lower boiling point gas of primary value, comprising precluding the need to distill the feed gas stream by the steps of:
   (a) providing a feed gas stream which is pressurized and cooled to a predetermined pressure and temperature;
   (b) providing an absorption column and a supply of substantially pure liquid carbon dioxide absorbent at substantially said predetermined pressure and temperature;
   (c) introducing absorbent from said supply thereof and feed gas stream into said absorption column for separating of said hydrogen sulfide and carbonyl sulfide from said lower boiling point gas;
   (d) contacting said feed gas stream in said absorption column with a countercurrent flow of absorbent in an amount sufficient, but not exceeding that required, to absorb and entrain substantially all of said hydrogen sulfide present in the gas stream and thereby also to absorb and entrain substantially all of said carbonyl sulfide in the gas stream while maintaining most of the absorbent in the liquid state at substantially said pressure and temperature, the balance of the absorbent being vaporized by the heat of condensation of the absorbed gas;
   (e) withdrawing from said absorption column a substantially completely desulfurized residual gas stream containing said relatively lower boiling point gas and a mixture of the still liquid absorbent and gases absorbed or entrained therewith; and (f) recovering substantially pure carbon dioxide from said desulfurized residual gas stream to concentrate further said relatively lower boiling point gas.

27. A process according to claim 26, in which at least a portion of the recovered carbon dioxide of step (f) is returned to said absorption column for reuse as absorbent.

28. A process according to claim 26, in which both the feed gas stream and liquid carbon dioxide absorbent are brought into contact in step (d) at substantially the same temperature and pressure and said temperature is substantially the dew point temperature of carbon dioxide in the feed gas stream at that pressure.

29. A process according to claim 26, in which the substantially completely desulfurized residual gas stream withdrawn from said absorption column in step (e) is cooled to condense carbon dioxide therefrom and the so-condenzed carbon dioxide reflux is returned to the process and used as part of the absorbent in step (d).

30. A process according to claim 26, in which step (d) is performed by withdrawing the substantially completely desulfurized residual gas stream from the top of said absorption column and the mixture of still liquid absorbent and gases absorbed or entrained therewith from the bottom of the column.

31. A process according to claim 26, in which the mixture of still liquid absorbent and gases absorbed or entrained therewith withdrawn from said absorption column in step (e) is processed to recover carbon dioxide therefrom and leave a mixture enriched in sulfur-containing gas, and carbon dioxide separated from said mixture is used in step (f) as a refrigerant for cooling the substantially completely desulfurized residual gas stream and recovering carbon dioxide.

32. A process according to claim 31, in which additional carbon dioxide separated from said mixture is also used as absorbent in step (d).

33. A process according to claim 26, in which said relatively lower boiling point gas comprises a major portion of said feed gas stream.

34. A process according to claim 26, in which said feed gas stream includes at least one additional gas of relatively lower boiling point selected from the group consisting of hydrogen, carbon monoxide, nitrogen, and methane, and said relatively lower boiling point gases comprise a major and portion of said feed gas stream.

35. A process according to claim 26, in which said feed gas stream consists essentially of hydrogen, carbon monoxide, nitrogen, and methane, together with said hydrogen sulfide, carbonyl sulfide, and carbon dioxide.

36. A process according to claim 26, in which step (a) includes cooling said feed gas stream to said predetermined temperature.

37. A process for treating a feed gas stream comprising relatively high boiling point gases including carbonyl sulfide and a relatively lower boiling point gas of primary value, comprising precluding the need to distill the feed gas stream by the steps of:

(a) providing a feed gas stream which is pressurized and cooled to a predetermined pressure and temperature;

(b) providing an absorption column and a supply of substantially pure liquid carbon dioxide absorbent at substantially said predetermined pressure and temperature;

(c) determining an effective flow range of absorbent equal to from about 70% to about 140% of the flow which would be required to absorb and entrain substantially all hydrogen sulfide in an otherwise indentical feed gas stream except for the substitution of hydrogen sulfide for carbonyl sulfide;

(d) introducing absorbent from said supply thereof and said feed gas stream into said absorber for separation of said carbonyl sulfide from the gas stream;

(e) countercurrently contacting said feed gas stream in said absorber with absorbent at a flow within said effective flow range to absorb and entrain substantially all carbonyl sulfide in the feed gas stream while maintaining most of the absorbent in the liquid state at substantially said pressure and temperature, the balance of the absorbent being vaporized by the heat of condensation; and (f) withdrawing from said absorption column a substantially completely desulfurized residual gas stream containing said relatively lower boilding point gas and a mixture of the still liquid absorbent and gases absorbed or entrained therewith.

38. A process as set forth in claim 37, wherein said effective flow range determined in step (c) is equal to from about 70% to about 120% of that needed to absorb and entrain all hydrogen sulfide.

39. A process according to claim 37, in which said relatively lower boiling point gas comprises a major portion of said feed gas stream.

40. A process according to claim 37, in which said feed gas stream includes at least one additional gas of relatively lower boiling point selected from the group consisting of hydrogen, carbon monoxide, nitrogen, and methane, and said relatively lower boiling point gases comprise a major portion of said feed gas stream.

41. A process as set forth in claim 37, wherein said feed gas stream also includes hydrogen sulfide, and said effective flow range determined in step (c) is equal to from about that needed to absorb and entrain substantially all of the hydrogen sulfide to about 140% of that flow.

42. A process as set forth in claim 37, wherein said feed gas stream also includes hydrogen sulfide, and said effective flow range determined in step (c) is equal to from about that needed to absorb and entrain substantially all of the hydrogen sulfide to about 120% of that flow.

43. A process according to claim 42, in which said relatively lower boiling point gas comprises a major portion of said feed gas stream.

44. A process according to claim 42, in which said feed gas stream includes at least one additional gas of relatively lower boiling point selected from the group consisting of hydrogen, carbon monoxide, nitrogen, and methane, and said relatively lower boiling point gases comprise a major portion of said feed gas stream.

* * * * *